(12) United States Patent
Gardner et al.

(10) Patent No.: US 10,646,207 B2
(45) Date of Patent: May 12, 2020

(54) BIOPSY SAMPLE STORAGE CONTAINER AND RELATED SAMPLER

(71) Applicant: SNPSHOT TRUSTEE LIMITED, Auckland (NZ)

(72) Inventors: Michael Stuart Gardner, Auckland (NZ); Roy Victor Bladen, Auckland (NZ)

(73) Assignee: SNPSHOT TRUSTEE LIMITED, Auckland (NZ)

( * ) Notice: Subject to any disclaimer, the term of this patent is extended or adjusted under 35 U.S.C. 154(b) by 570 days.

(21) Appl. No.: 15/030,205

(22) PCT Filed: Oct. 17, 2014

(86) PCT No.: PCT/IB2014/065397
§ 371 (c)(1),
(2) Date: Apr. 18, 2016

(87) PCT Pub. No.: WO2015/056229
PCT Pub. Date: Apr. 23, 2015

(65) Prior Publication Data
US 2016/0235391 A1     Aug. 18, 2016

(30) Foreign Application Priority Data

Oct. 18, 2013 (NZ) .................................. 616807
Jun. 5, 2014 (NZ) .................................. 625902
Jun. 5, 2014 (NZ) .................................. 625904

(51) Int. Cl.
*A61B 10/02* (2006.01)
*A01K 11/00* (2006.01)
(Continued)

(52) U.S. Cl.
CPC .......... *A61B 10/0266* (2013.01); *A01K 11/00* (2013.01); *A01K 11/003* (2013.01);
(Continued)

(58) Field of Classification Search
CPC combination set(s) only.
See application file for complete search history.

(56) References Cited

U.S. PATENT DOCUMENTS 4,976,925 A    12/1990   Porcher
6,235,036 B1 *  5/2001   Gardner ............... A01K 11/002
                                                606/117
(Continued)

FOREIGN PATENT DOCUMENTS

AU      2009329486      11/2014
CN      1275894         12/2000
(Continued)

OTHER PUBLICATIONS

Office Action from the US Patent and Trademark Office for U.S. Appl. No. 14/896,325 dated Sep. 27, 2018 (18 pages).
(Continued)

*Primary Examiner* — Sean P Dougherty
(74) *Attorney, Agent, or Firm* — Michael Best & Friedrich LLP

(57) ABSTRACT

A storage container to receive and store a biopsy sample of an organism, held by a biopsy sample collector, the storage container comprising a container body defining a containment region with an open end, and a container cap removably located at the open end to seal the containment region, the cap including a passage that is closed by a closure that is able to be ruptured to allow a biopsy sample retaining biopsy sample collector to thereat enter the containment region so that the sample can be stored in the containment region and the sample collector can seal the passage.

9 Claims, 28 Drawing Sheets

(51) Int. Cl.
      *A61B 10/00*        (2006.01)
      *A61B 90/00*        (2016.01)
(52) U.S. Cl.
      CPC ........ *A01K 11/006* (2013.01); *A61B 10/0096*
              (2013.01); *A61B 10/0283* (2013.01); *A61B*
                *2010/0208* (2013.01); *A61B 2010/0225*
              (2013.01); *A61B 2090/081* (2016.02); *A61B*
               *2503/40* (2013.01); *A61B 2562/08* (2013.01)

(56) References Cited

U.S. PATENT DOCUMENTS

| | | | |
|---|---|---|---|
| 6,631,650 | B1 | 10/2003 | Espinosa |
| 6,659,338 | B1 | 12/2003 | Dittmann et al. |
| 6,696,923 | B2 | 2/2004 | Ishii et al. |
| 6,753,759 | B2 | 6/2004 | Stegmaier et al. |
| 6,947,866 | B2 | 9/2005 | Staab |
| 6,968,639 | B2 | 11/2005 | Destoumieux |
| 7,235,055 | B2 * | 6/2007 | Pfistershammer ... A01K 11/002 600/562 |
| 7,467,760 | B2 | 12/2008 | Schieli et al. |
| 7,528,725 | B2 | 5/2009 | Stewart |
| 7,764,177 | B2 | 7/2010 | Stewart |
| 7,764,181 | B2 | 7/2010 | Stewart et al. |
| 7,791,409 | B2 | 9/2010 | Arrigo |
| 7,936,272 | B2 | 5/2011 | Stewart |
| 8,070,757 | B2 | 12/2011 | Eadie |
| 8,159,291 | B2 | 4/2012 | Arrigo |
| 8,361,416 | B2 | 1/2013 | Berner |
| 8,581,705 | B2 | 11/2013 | Stewart |
| 8,668,655 | B2 | 3/2014 | Destoumieux |
| 8,763,287 | B2 | 7/2014 | Hilpert |
| 8,854,188 | B2 | 10/2014 | Stewart |
| 9,554,557 | B2 * | 1/2017 | Nehls ................... A01K 11/003 |
| 10,299,768 | B2 * | 5/2019 | Gardner ............ A61B 10/0266 |
| 2002/0120216 | A1 | 8/2002 | Fritz et al. |
| 2004/0103567 | A1 | 6/2004 | Destoumieux |
| 2004/0167429 | A1 | 8/2004 | Roshdieh |
| 2004/0167430 | A1 | 8/2004 | Roshdieh |
| 2004/0232323 | A1 | 11/2004 | Bosco et al. |
| 2005/0038355 | A1 | 2/2005 | Gellman et al. |
| 2005/0228310 | A1 | 10/2005 | Pfistershammer |
| 2005/0256425 | A1 * | 11/2005 | Prusiner ................. A61B 10/02 600/567 |
| 2005/0272057 | A1 | 12/2005 | Abrahamsen |
| 2007/0239067 | A1 | 10/2007 | Hibner |
| 2008/0064983 | A1 * | 3/2008 | Stromberg ........... A01K 11/003 600/567 |
| 2008/0170967 | A1 | 7/2008 | Itoh |
| 2008/0227662 | A1 * | 9/2008 | Stromberg ........... A01K 11/003 506/39 |
| 2008/0228105 | A1 | 9/2008 | Howell et al. |
| 2009/0270878 | A1 | 8/2009 | Eadie |
| 2010/0016758 | A1 | 1/2010 | Hilbert |
| 2010/0084364 | A1 * | 4/2010 | Martin ................... B65D 41/34 215/201 |
| 2010/0160830 | A1 | 6/2010 | Schmiedl |
| 2010/0168616 | A1 | 7/2010 | Schraga et al. |
| 2010/0210011 | A1 | 8/2010 | Hilbert |
| 2010/0286556 | A1 | 11/2010 | Decaluwe et al. |
| 2010/0291662 | A1 | 11/2010 | Berner |
| 2011/0127177 | A1 | 6/2011 | Hostettler |
| 2011/0269228 | A1 | 11/2011 | Decaluwe |
| 2011/0295148 | A1 * | 12/2011 | Destoumieux ....... A01K 11/003 600/564 |
| 2012/0010526 | A1 * | 1/2012 | Hilpert ................. A01K 11/003 600/564 |
| 2012/0016263 | A1 | 1/2012 | Hilpert |
| 2013/0040358 | A1 | 2/2013 | Woods et al. |
| 2013/0204159 | A1 | 8/2013 | Destoumieux |
| 2013/0211287 | A1 | 8/2013 | Decaluwe |
| 2013/0211416 | A1 | 8/2013 | Teychene |
| 2014/0034183 | A1 * | 2/2014 | Gross ................. B65D 51/2864 141/1 |
| 2014/0249449 | A1 | 9/2014 | Hilpert |
| 2015/0112225 | A1 | 4/2015 | Prow et al. |
| 2015/0226646 | A1 | 8/2015 | Lardi et al. |
| 2016/0007567 | A1 | 1/2016 | Decaluwe et al. |

FOREIGN PATENT DOCUMENTS

| | | |
|---|---|---|
| CN | 102933157 | 2/2013 |
| CN | 103052313 | 4/2013 |
| DE | 19835014 | 8/1999 |
| DE | 20022647 | 1/2002 |
| EP | 0016236 | 10/1980 |
| EP | 982688 | 3/2000 |
| EP | 1014861 | 7/2000 |
| EP | 1060662 | 12/2000 |
| EP | 1318718 | 6/2003 |
| EP | 1781086 | 9/2007 |
| EP | 1920651 | 5/2008 |
| EP | 1809096 | 2/2009 |
| EP | 2066170 | 6/2009 |
| EP | 2068718 | 6/2009 |
| EP | 2160093 | 3/2010 |
| EP | 2168207 | 3/2010 |
| EP | 2249966 | 11/2010 |
| EP | 2265109 | 12/2010 |
| EP | 2307136 | 4/2011 |
| EP | 2355653 | 8/2011 |
| EP | 2378863 | 10/2011 |
| EP | 2384618 | 11/2011 |
| EP | 2384619 | 11/2011 |
| EP | 1718142 | 10/2012 |
| EP | 2579781 | 4/2013 |
| EP | 2579782 | 4/2013 |
| EP | 2597944 | 6/2013 |
| EP | 2736324 | 6/2014 |
| EP | 2770819 | 9/2014 |
| FR | 2939281 | 6/2010 |
| GB | 2358061 | 7/2001 |
| GB | 2482036 | 1/2012 |
| IN | 201200015 | 5/2012 |
| JP | 2006026227 | 2/2007 |
| JP | 2012511310 | 5/2012 |
| JP | 2012514201 | 6/2012 |
| JP | 2012526966 | 11/2012 |
| JP | 2013079859 | 5/2013 |
| NZ | 503521 | 12/2002 |
| NZ | 575341 | 1/2012 |
| NZ | 593039 | 12/2012 |
| NZ | 596853 | 2/2014 |
| NZ | 608927 | 11/2014 |
| SU | 946387 | 7/1982 |
| WO | 200051496 | 9/2000 |
| WO | 2001040762 | 6/2001 |
| WO | 2002023980 | 3/2002 |
| WO | WO 2002039810 | 5/2002 |
| WO | WO 2005101273 | 10/2005 |
| WO | 2006000869 | 1/2006 |
| WO | 2007013820 | 2/2007 |
| WO | 2008037802 | 4/2008 |
| WO | 2008040692 | 4/2008 |
| WO | 2008101497 | 8/2008 |
| WO | 2009010658 | 1/2009 |
| WO | WO 2009008861 | 1/2009 |
| WO | 2009046957 | 4/2009 |
| WO | 2009095178 | 8/2009 |
| WO | 2009127541 | 10/2009 |
| WO | WO 2009120206 | 10/2009 |
| WO | 2010012446 | 2/2010 |
| WO | 2010066475 | 6/2010 |
| WO | 2010070129 | 6/2010 |
| WO | 2010070130 | 6/2010 |
| WO | WO 2010066475 | 6/2010 |
| WO | WO 2010070130 | 6/2010 |
| WO | WO 2011044585 | 4/2011 |
| WO | 2011073359 | 6/2011 |
| WO | 2011154233 | 12/2011 |
| WO | 2011154510 | 12/2011 |
| WO | 2012013429 | 2/2012 |
| WO | 2013014034 | 1/2013 |

(56) References Cited

FOREIGN PATENT DOCUMENTS

| WO | 2013060690 | 5/2013 |
|---|---|---|
| WO | WO 2013155557 | 10/2013 |
| WO | 2014153181 | 9/2014 |
| WO | WO 2015014461 | 2/2015 |
| WO | WO 2015158787 | 10/2015 |
| WO | WO 2016016204 | 2/2016 |
| WO | WO 2016073754 | 5/2016 |

OTHER PUBLICATIONS

Office Action from the US Patent and Trademark Office for U.S. Appl. No. 14/896,322 dated Jun. 12, 2018 (13 pages).
International Search Report for Application No. PCT/IB2014/065397 dated Feb. 26, 2015 (3 pages).
International Preliminary Report on Patentability for Application No. PCT/IB2014/065397 dated Feb. 3, 2016 (4 pages).
International Search Report for Application No. PCT/IB2014/065394 dated Feb. 9, 2015 (3 pages).
International Preliminary Report on Patentability for Application No. PCT/IB2014/065394 dated Feb. 3, 2016 (4 pages).
International Search Report for Application No. PCT/IB2014/065395 dated Feb. 10, 2015 (5 pages).
International Preliminary Report on Patentability for Application No. PCT/IB2014/065395 dated Sep. 2, 2015 (5 pages).
International Search Report for Application No. PCT/IB2014/065393 dated Feb. 3, 2016 (6 pages).
International Preliminary Report on Patentability for Application No. PCT/IB2014/065393 dated Feb. 3, 2016 (7 pages).
International Search Report for Application No. PCT/IB2014/065396 dated Feb. 19, 2015 (6 pages).
Written Opinion from the International Searching Authority for Application No. PCT/IB2014/065396 dated Feb. 19, 2015 (7 pages).
Office Action from the US Patent and Trademark Office for U.S. Appl. No. 15/030,211 dated Nov. 20, 2018 (12 pages).
Office Action from the US Patent and Trademark Office for U.S. Appl. No. 15/030,203 dated Feb. 1, 2019 (12 pages).
Office Action from the US Patent and Trademark Office for U.S. Appl. No. 14/896,322 dated Feb. 4, 2019 (13 pages).

* cited by examiner

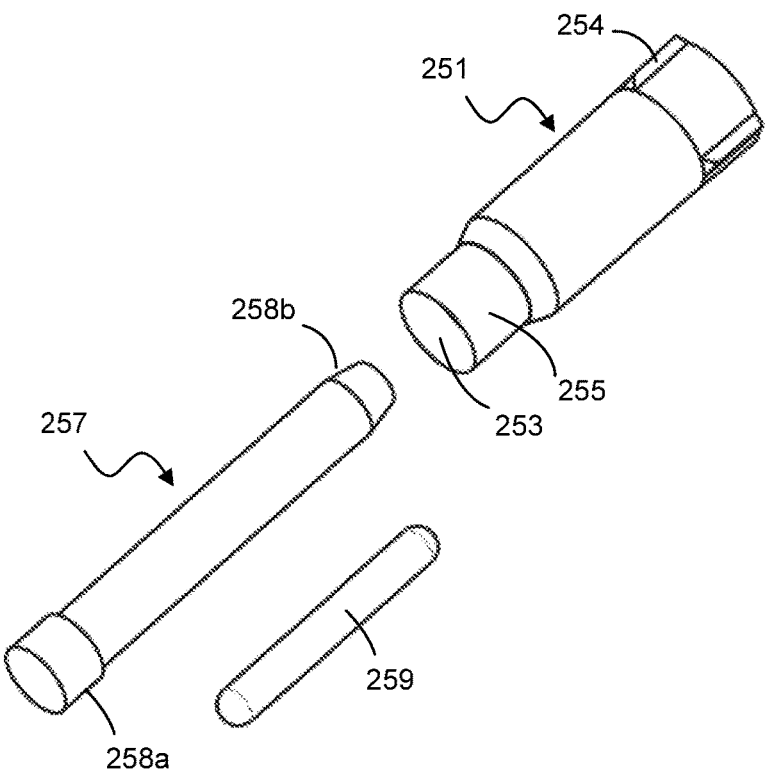
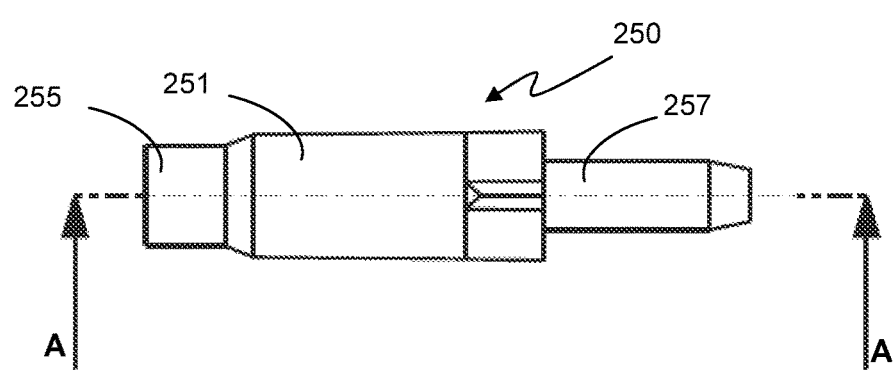
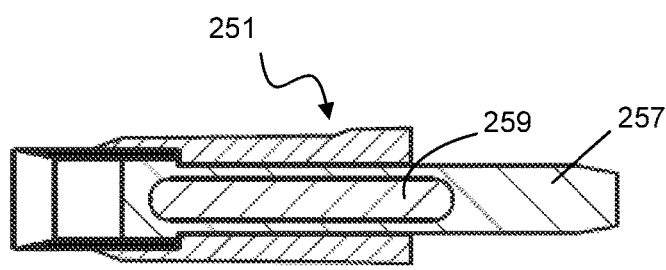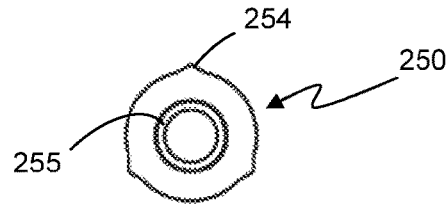

BIOPSY SAMPLE STORAGE CONTAINER AND RELATED SAMPLER

CROSS-REFERENCE TO RELATED APPLICATIONS

This application is a national stage filing under 35 U.S.C. § 371 of International Application No. PCT/IB2014/065397, filed Oct. 17, 2014, which claims foreign priority to New Zealand Application No. 625904, filed Jun. 5, 2014, New Zealand Application No. 625902, filed Jun. 5, 2014, and New Zealand Application No. 616807, filed Oct. 18, 2013. The entire contents of all four applications are incorporated herein by reference.

FIELD OF THE INVENTION

The invention relates to a biopsy sample handling method and related storage container.

BACKGROUND OF THE INVENTION

To improve the tracking of livestock and to facilitate DNA testing, tissue samples may be collected from animals. A tissue sample may be taken from an animal at any time and is often taken at the same time as placing an identification tag on the animal. The tissue sample is usually cut from an animal using a tissue sampling device and is placed in a storage container for laboratory analysis.

US patent publications US2011/0295148 and US2013/0204159 describe a tissue sampler in the shape of a clamp and comprising a pair of jaws that move toward each other to take a tissue sample. A cutting element is located in one of the jaws and is forced through an animal's ear, for example, to cut a plug of tissue from the ear as the jaws are clamped together using a first actuation action. A plunger is used to push the tissue sample out of the cutting element and into a storage tube held by the other jaw of the tissue sampler. The storage tube has a closed end and an opposing end. The tube comprises an aperture through which the tissue sample is pushed by the plunger. The plunger remains in the aperture of the storage tube cap to seal the tube before the tube is removed from the device and taken away for analysis.

After the storage tube is removed, the cutting element needs to be removed from the sampler because a different cutting element needs to be used for each tissue sample to prevent contamination of the tissue sample. The cutting element can be automatically ejected through a second actuation action of the sampler. The cutting element is then discarded onto the ground or into a refuse container. The cutting elements are sharp and so handling the cutting element carries a risk of being cut. Discarding the cutting element on the ground also carries this risk.

When the storage tube is removed for analysis, it is necessary for the cap of the storage tube (containing the plunger) to be removed before the tissue sample that has already been dispensed into the bottom of the tube can be extracted for analysis or being analysed in the tube. Because of the design of the tube and cap, each cap is removed individually in the laboratory, which is a time consuming and therefore costly process.

The sample, having been pushed into the bottom of the tube is also more exposed and hence subject to drying or contamination.

It is an object of the present invention to provide a biopsy sample handling method and related storage container that addresses the above disadvantages and/or that will at least provide the public with a useful choice.

SUMMARY OF THE INVENTION

In a first aspect the present invention may broadly be said to be a storage container to receive and store a biopsy sample of an organism, held by a biopsy sample collector, said storage container comprising:

a. a container body defining a containment region with an open end, b. a container cap removably located at the open end to seal the containment region, the cap including a passage that is closed by a closure that is able to be ruptured to allow a biopsy sample retaining biopsy sample collector to thereat enter the containment region so that the sample can be stored in the containment region and said sample collector can seal the passage.

Preferably the passage and/or seal are adapted and configured to act as a die and cooperate with a punch of said sample collector that includes a cutter at one end to penetrate the organism and pass there though and into said passage to remove a sample with the cutter.

Preferably a tamper evident indicator is provided to indicate separation of the cap from the container body.

Preferably the closure is able to be ruptured by the biopsy sample collector.

Preferably the closure is able to be ruptured by said cutter of the punch of the storage container.

Preferably this occurs as the same time as the separation of the sample from the organism.

Preferably the closure of the cap is a membrane.

Preferably the membrane is integrally formed with the cap and fully seals the passage prior to being ruptured.

Preferably the closure is able to separate from the cap upon rupturing.

Preferably the closure is able split open upon rupturing yet at least in part be retained to said cap.

Preferably the cap is adapted and configured to receive the sample collector and hold said sample collector after rupturing of said closure and entry of said sample into the containment region.

Preferably the cap is adapted and configured to prevent the sample collector from being removed there from after rupturing of said closure and entry of said sample into the containment region.

Preferably the passage is shaped and dimensioned to result in a wedging of the sample collector therein to prevent the removal of the sample collector from the cap after rupturing of said closure and entry of said sample into the containment region.

Preferably the passage includes a lip or recess or grove or slot to thereat retain a complementary enlargement of the sample collector and prevent its removal from the cap after rupturing of said closure and entry of said sample into the containment region.

Preferably the passage is of a depth and width to receive the sample collector in a manner so that it cannot be grasped by person in a manner to remove it from the cap, when it has after ruptured said closure and said sample has entered into the containment region.

Preferably the passage is shaped to accommodate at least part of the sample collector therein.

Preferably the passage is shaped to snugly accommodate the sample collector.

Preferably the passage is shaped to accommodate the sample collector, after rupturing of said closure and entry of said sample into the containment region, in a manner so that the sample collector seals the passage.

Preferably in the cap presents a sample cutting surface to cooperate with the sample collector in cutting a sample from the specimen to be sample.

Preferably the cutting surface is presented for a cutter of the sample collector to press on or pass by in a shearing action to facilitate in the removal of a sample from the specimen to be sampled.

Preferably the surface is of the closure.

Preferably the surface and passage together act as a die for the cutter to cooperate with in removing the sample.

Preferably the container body is a tube having a closed base end opposed the opposed end and a side wall or walls extending there between.

Preferably the tamper evident indicator is a tamper evident ring that is integrally formed with one of the container body and cap and is engaged to the other of said cap or container body in a manner so that upon separation of the cap from the container body, the ring at least in part becomes disconnected from the container body or cap with which it is integrally formed.

Preferably the tamper evident indicator is a shrink wrap located about the interface of the cap and container body so that separation of the cap from the container body results in the shrink wrap rupturing.

Preferably the tamper evident indicator is an adhesive label that extends across the interface of the cap and container body and is adapted and configured to rupture upon separation of the cap and container body.

Preferably the compartment contains a preservative.

Preferably at least one of the container body and cap includes at least one of an EID and machine readable code (such as a barcode).

Preferably the storage container is a biopsy sample storage container.

In a further aspect the present invention may broadly be said to be a storage container to receive and store a biopsy sample held by a biopsy sample collector, said storage container comprising a container body defining a closed containment region, there being a passage leading to said containment region that is closed by a closure that is able to be ruptured to create an opening into said containment region to allow a biopsy sample retaining biopsy sample collector to threat enter the containment zone so that the sample can become stored in the containment zone, held by said collector, and where said collector closes the opening.

Preferably the passage is defined by a cap that is releasably engaged to the container body.

Preferably the sample collector to be used with the container is to take and hold a biopsy sample from an organism upon being driven by an actuator through said organism, said collector comprising:

a punch that includes a cutter with a cutting edge formed at a cutting end of the punch to remove and retain a biopsy sample and a plunger retained to said punch in a manner to allow it to move relative said cutter to remove a cutter retained biopsy sample from the cutter.

Preferably the plunger is mounted to said punch.

Preferably the plunger is secured to said punch in a movable manner.

Preferably the plunger is not caused to be moved relative said punch by said actuator upon driving of the collector into the organism.

Preferably the plunger is able to move relative said punch but is not able to be removed there from.

Preferably the plunger is actuatable to remove the cutter retained biopsy sample after sampling.

Preferably the punch includes a passage there through extending from the cutting edge of said cutter to an opposed end of said punch, said plunger retained to said punch at said passage to be guided for movement thereby.

Preferably an EID is secured to one of said plunger and punch.

Preferably the EID is embedded in said plunger, preferably in a manner so it cannot be removed yet can be read.

In a further aspect the present invention may broadly be said to be a sampler tool to hold a (i) storage container as claimed in claim 1 and (ii) a sample collector to take and hold and store a biopsy sample from an organism said collector comprising a punch that includes a cutter with a cutting edge formed at a cutting end of the punch to remove and retain a biopsy sample the tool comprising a body carrying a ram to drive the collector and able to be actuated for move along a path relative the body between a first position aligned to drive the collector from a primed position separated from said container with part of said organism intermediate, and push the collector through part of said organism and a second position where said cutter has been so pushed through by said ram, to remove a sample from said organism and into the storage container, the collector retained after sampling at the passage and plugging the passage into the storage container.

Preferably the collector includes a plunger retained to said punch in a manner to allow it to move relative said cutter to remove a cutter retained biopsy sample from the cutter.

Preferably said ram acts on said punch of said collector in a manner to not be able to cause relative movement of the plunger relative said punch.

Preferably the ram, nor any parts that move with it can cause the plunger to be moved relative said punch.

Preferably the collector remains retained at the passage after the storage container and collector are removed from the sample tool.

Preferably the end of the ram includes a recess into which the plunger, when projecting from said punch, can be accommodated during driving of said collector, so as to prevent the ram from moving the plunger relative the punch.

Preferably the sampler tool during movement of the collector by said ram, cannot cause the plunger to be moved relative the punch.

Preferably the ram is an elongate member that is axially aligned with said collector when moving from its first position to its second position.

In a further aspect the present invention may broadly be said to be an assembly of a storage container as hereinbefore described and a sample collector comprising a punch that includes a cutter with a cutting edge formed at a cutting end of the punch that has removed and retains a biopsy sample, the passage of the cap sealed by said collector, said collector holding said sample and locating it in said containment region.

Preferably the collector includes a plunger retained to said punch in a manner to allow it to move relative said cutter to remove a cutter retained biopsy sample from the cutter.

Preferably the plunger protrudes from said punch.

Preferably the plunger protrudes from the punch to allow it to pushed after the sample is located in said containment region, to eject the sample from said collector.

Preferably the ejecting causes the sample to contact said container body.

Preferably the ejecting is done after the cap has been removed from said container body after sample taking.

Preferably the container body is a tube.

Preferably the cap is a screw cap.

In a further aspect the present invention may broadly be said to be a die to cooperate with a punch to remove and store a tissue sample from an animal said die forming part of a cap removably engaged to a storage container body together defining a sealed containment region, said die including a passage leading through the cap into the containment region and into which a said punch becomes secured upon removal of a sample from a said animal for delivery into and storage of said sample in said containment region.

Preferably said passage is sealed by said punch upon sample delivery.

Preferably said cap is threadingly engaged to said container body.

Preferably said passage is sealed by a punch rupturable seal.

Preferably the passage is adapted and configured to receive and hold a said punch and thereat cause a shear cutting action of the sample from said organism.

In a further aspect the present invention may broadly be said to be a punch and die set for removing a tissue sample from an animal said set comprising a punch to be driven through part of said animal and a die to cooperate with said punch in removing a sample from said animal, said die being a removable cap of or for a storage container having a storage container body that together with the cap defines a containment region, said cap including a passage there through to provide accesses into the containment region and into which said punch becomes secured upon removal of a sample from a said animal for delivery into and storage of said sample in said containment region.

Preferably said passage and said punch are adapted and configured so that upon sample delivery said passage is plugged by said punch to seal said containment region and secure said sample therein.

Preferably said cap is threadingly engaged to said container body.

Preferably said passage is sealed by a punch rupturable seal prior to sampling.

Preferably said containment region is sealed prior to said punch entering said passage.

Preferably the passage is adapted and configured to (a) receive and hold a said punch and (b) thereat cause a shear cutting action of the sample from said organism.

Preferably the punch is retained by said die at least partially in said passage.

Preferably the die is secured to said container body with a tamper evident indicator provided to indicate when said die has been removed from said body.

In a further aspect there is provided a sampler tool comprises:

a cutting/penetration zone for receiving a body of tissue to be sampled, a ram situated at a first side of the penetration zone able to be actuated to move along a path between a withdrawn position and an advanced position, a sample collector that can cut a biopsy sample from tissue interposed in the penetration zone, and a container as herein described that can receive the sample collector, the sample collector and the container being initially located on opposite sides of the penetration zone, a disposable shield initially located between the ram (with the ram in the withdrawn position) and the penetration zone, advance action of the ram from the withdrawn to the advanced position bringing together the sample collector and container at side of the penetration zone away from the ram, and bringing the disposable shield into the penetration zone, withdrawal action of the ram from the advanced position to the withdrawn position withdrawing the disposable shield to the first side of the penetration zone, leaving the tissue free to leave the penetration zone, such that in use in collecting a sample the shield contacts tissue surfaces and the ram does not contact tissue surfaces.

Preferably the disposable shield is a sleeve to receive a leading end of the ram, and protect the leading end of the ram from contacting the tissue surfaces to the extent that the leading end of the ram enters the penetration zone.

Preferably the sleeve is open through to both ends such that the leading end of the ram may act directly on the sample collector or container.

Preferably the disposable shield spaces the ram from the sample collector or container and the ram acts to bring the sample collector and container together by acting on the shield which acts on the sample collector or container.

Preferably the travel of the ram is limited so that the ram cannot enter the penetration zone.

Preferably the disposable shield releasably connects to a leading end of the ram as the ram advances, and disconnects as or before the ram reaches the withdrawn position on withdrawal.

Preferably the sample collector is initially located between the ram and the penetration zone.

Preferably the disposable shield is releasably fitted to the sample collector in an initial condition, and releasably connects to a leading end of the ram as the ram advances, disconnects from the sample collector as the ram begins to withdraw, and disconnects from the ram as or before the ram reaches the withdrawn position on withdrawal.

Preferably the connection of the ram to the shield is stronger than the connection of the shield to the sample collector such that withdrawal of the ram reliably releases the shield from the sample collector.

Preferably the sampler includes a magazine loading zone between the ram (in the withdrawn position) and the penetration zone, and a magazine locatable in the magazine loading zone, the magazine carrying a plurality of sample collectors to be selectively presented in the path of the ram and be actuated by the ram to be moved from the magazine through the penetration zone, each sample collector being stored in the magazine in association with a respective disposable shield, the disposable shield returning to the magazine on withdrawal of the ram after actuation.

Preferably the shield releases from the ram upon full withdrawal of the shield into the magazine and by continuing withdrawal motion of the ram.

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

As used herein the term "and/or" means "and" or "or", or both.

As used herein "(s)" following a noun means the plural and/or singular forms of the noun.

The term "comprising" as used in this specification means "consisting at least in part of". When interpreting statements in this specification which include that term, the features, prefaced by that term in each statement, all need to be present but other features can also be present. Related terms such as "comprise" and "comprised" are to be interpreted in the same manner.

The entire disclosures of all applications, patents and publications, cited above and below, if any, are hereby incorporated by reference.

Any reference to prior art documents in this specification is not to be considered an admission that such prior art is widely known or forms part of the common general knowledge in the field.

BRIEF DESCRIPTION OF THE DRAWINGS

Preferred forms of the invention will now be described by way of example only and with reference to the accompanying drawings, in which:

FIG. 1a is an exploded view of one form of collector;

FIG. 1b is a side view of one form of the collector;

FIG. 1c is a cross-sectional side view of the collector taken along line A-A of FIG. 1b;

FIG. 1d is an end view of the collector of FIG. 1b;

FIG. 2b is a side view of the punch of FIG. 2a;

FIG. 2c is an end view showing the pushing end of the punch of FIG. 2a;

FIG. 2e is an end view showing the cutting end of the punch of FIG. 2a;

FIG. 3b is a side view of the body of FIG. 3a;

FIG. 3c is a cross-sectional side view of the body taken along line A-A of FIG. 3a;

FIG. 3d is an end view of the closed second end of the body of FIG. 3a;

FIG. 15b is a cross sectional side view of the storage containers taken along the line AA of FIG. 15a;

DETAILED DESCRIPTION OF PREFERRED FORMS OF THE INVENTION

Figure 1E:
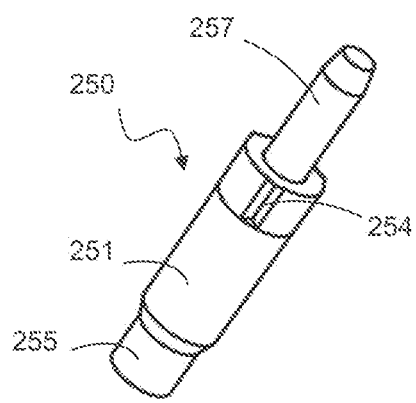
FIG. 1e is a perspective view of another form of the collector.
Figure 1F:
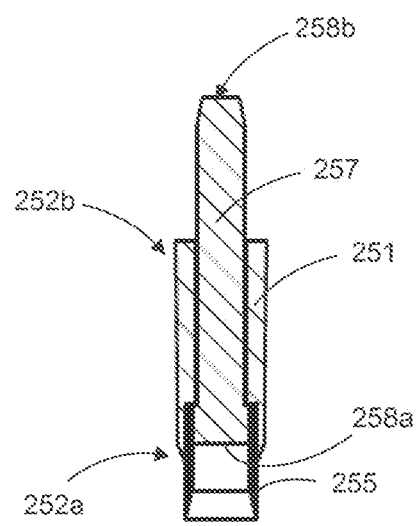
FIG. 1f is a cross-sectional side view of the collector of FIG. 1e.

Reference will now be made to a storage container to receive and store biopsy samples and its cooperation with a sample collector. Such samples may be from an organism such as plants or animals particularly, including pigs, goats, cattle, sheep, poultry, and fish. In a preferred form the sample is taken from the ear of an animal. In use, the storage container may be used with a collector that is also herein described and with a sampler to facilitate the taking and storing of a sample. Together the collector and container can collect and store a biopsy sample for later analysis.

The collector that may be used with the container will first be described.

FIGS. 1a to 1g show a preferred form of a collector 250. The collector can be used with the tissue sampler as will herein after be described or with any other suitable tissue sampler.

The collector 250 comprises a punch 251 having a body with a cutter 255 at a cutting end 252a of the punch 251. The punch 251 also has an opposing pushing end 252b. The body of the punch 251 preferably has a slot or bore 253. The bore 253 extends from one end of the punch to the other. It preferably extends along the length of the punch between the cutting end and the pushing end, as shown in FIGS. 2a to 2e. Preferably, the punch has an elongate straight body and the bore is centrally located within the body of the punch.

In one form, the outer surface of the body of the punch comprises guides in the form of one or more projections or recesses to help locate the punch within a cap of a storage container as will be described later. In the embodiment shown in FIGS. 2a to 2d, the guides comprise three evenly spaced ribs 254 that project from the pushing end 252b of the punch. A lead-in 254a may also be provided.

A cutter 255 is provided at the cutting end 252a of the punch to remove a sample from an organism. The cutter may be attached to the punch or it may be integral with the punch so that the cutter and punch are formed as a single part. The cutter 255 may be cylindrical. It may alternatively be of another shape suitable to remove a sample. The sample may for example be taken from the tip of the ear of an animal and the cutter may as a result be U or V shaped or other shape. It need not take a core sample but an edge sample instead. Being of a hollow section such as cylindrical does offer the added benefit of being able to retain the sample, as a plug, by the cutter. The cutter can remove a sample plug that ends up sitting in the cutter.

A free end of the cutter 255 is presented to form a cutting edge 255a. The cutter 255 preferably extends from and surrounds one end of the bore 253 of the punch at the cutting end of the punch body to form a projecting surrounding wall or walls. Preferably, the bore 253 of the punch is cylindrical so that the cutting edge is substantially circular. A sample holding section 256 is formed by the cutter, preferably within the projecting wall(s) of the cutter. In this way, the cutter provides a sample holding section 256 such as a bore. The bore is a blind bore terminated by the end of the plunger 257. It is aligned with the bore formed in the body of the punch. For the sake of simplicity, the bore 253 of the punch, when referred to in this specification, should be interpreted to include the bore formed in the body of the punch and the bore formed in the cutter because the two are preferably contiguous.

A plunger 257 is held at the bore 253 of the punch and forms part of the collector. In one form the plunger protrudes at least partially from the punch. In other forms it is contained entirely within the bore. Being within the bore helps protect it and prevent tampering therewith at least unless an appropriate tool is used.

The plunger preferably includes a machine readable electronic identity (EID) tag such as a radio frequency identity (RFID) tag. The RFID system may be selected according to the anticipated manufacturing and use conditions of the tissue sample collector. For example a typical passive tag, active reader, system operating at low frequency can provide robust identification devices suitable for embedding in molded plastic components at a unit cost that is appropriate. The tag 259 illustrated in FIGS. 1a and 1c is typical of the form of RFID tags of this type. However other systems, such as passive tag systems operating in the UH range can provide lower unit costs. Tags of this type are available that are claimed to be sufficiently robust for embedding in molded plastic components.

To work well with these small RFID tags, an RFID reader may be integrated to the tissue sampler, or mounted to the tissue sampler, immediately adjacent the position that a sample occupies at the time of use.

The plunger has a first end 258a and an opposing second end 258b.

The plunger 257 can be seen to extend into the bore 253 of the punch 251. The fit of the plunger in the bore is snug yet allowing for the plunger to slide relative the punch. In the preferred form the plunger outer surface is contiguous the inner surface of the bore. This ensure that a seal is created there between, preventing ingress of contaminants from the pushing end of the punch to the cutting end, through the bore.

The plunger and punch are in a sliding relationship with each other whether it is using a bore and pin like relationship or other. They are in a sliding relationship so that the sample can be pushed off the cutter.

The plunger in the preferred form extends into the bore of the punch and can push a plug of sample tissue from the sample holding section 256. This pushing may be to push the sample into a storage container with which the collector becomes associated after sample taking. It may occur at the time of sampling or well after such as in the laboratory at where the sample will be processed. In the lab the sample may be pushed off the cutter and into a test tube after the container has been removed from the collector retaining cap.

Figure 1G:
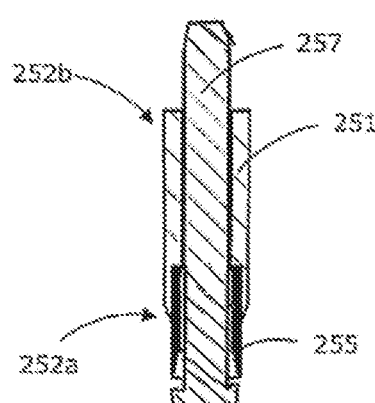
FIG. 1g is a view of the collector in a condition where the plunger is actuated.
Figure 2A:
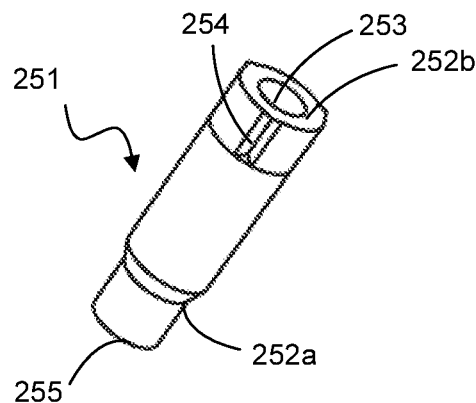
FIG. 2a is a perspective view of one form of punch for a collector.
Figure 2B:
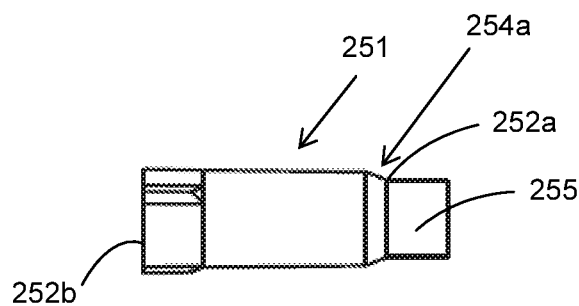
Figure 2C:
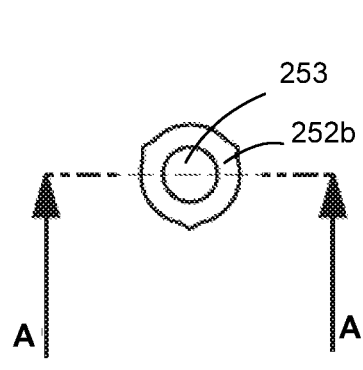
Figure 2D:
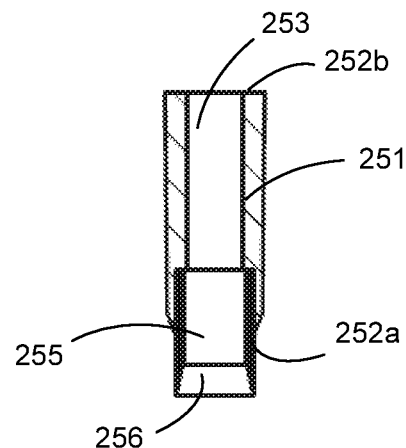
FIG. 2d is a side view of the punch taken along line A-A of FIG. 2c.
Figure 2E:
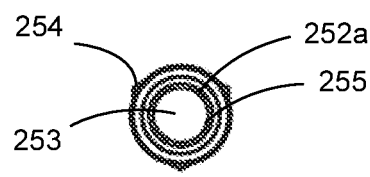
Figure 3A:
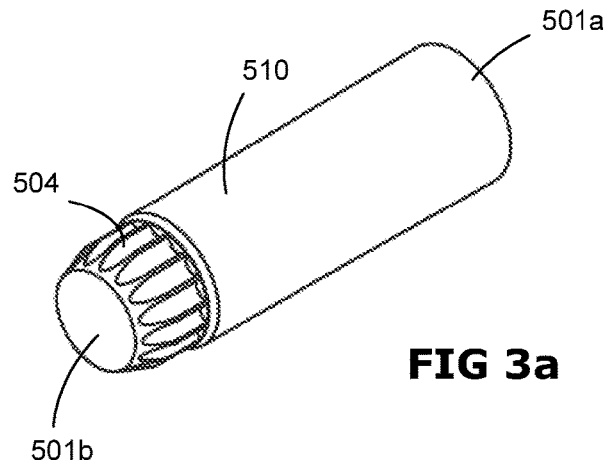
FIG. 3a is a perspective view of one form of storage body according to the invention.
Figure 3B:
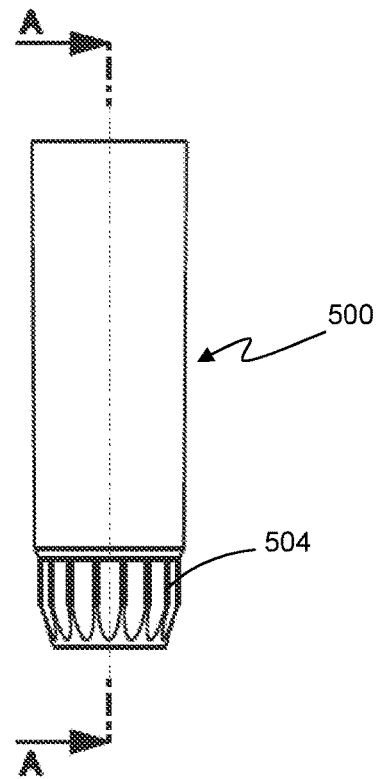
Figure 3C:
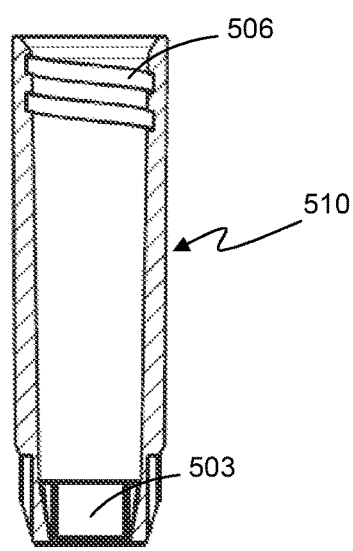
Figure 3D:
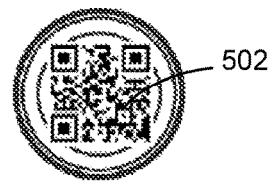
Figure 3E:
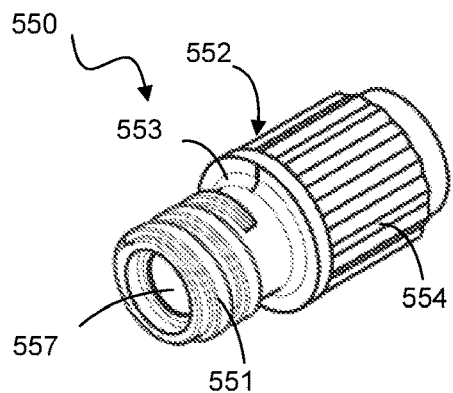
FIG. 3e is a perspective view of one form of cap for a storage container according to the invention.
Figure 3F:
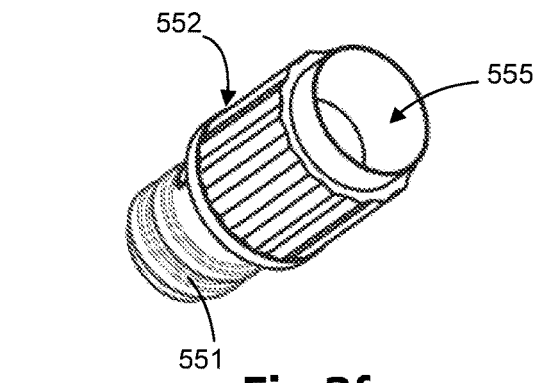
FIG. 3f is another perspective view of the cap of FIG. 3e.
Figure 3G:
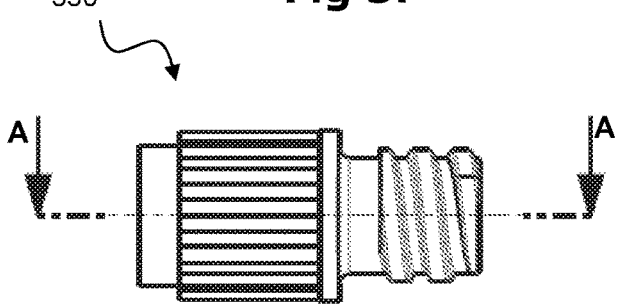
FIG. 3g is a side view of the cap of FIG. 3e.
Figure 3H:
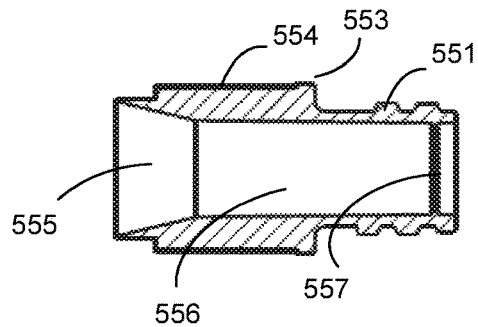
FIG. 3h is a cross-sectional side view of the cap of FIG. 3g.

The plunger is able to be positioned in an active position as shown in FIG. 1b and be moved to a plunged position as seen in FIG. 1g.

When the plunger is in an active position, ready for the collector to remove a sample from the cutter, the second end of the plunger may project from the pushing end of the punch and the first end of the plunger is held within the bore of the punch between the sample holding section and the pushing end of the punch. Preferably, at or near the first end 258a the plunger is enlarged or provides some form that creates and interference to the removal of the plunger from the punch in one direction. A similar enlargement (not shown) may be provided at or near the other end of the plunger. The or each enlargement helps prevent the removal of the plunger that may carry the RFID from the collector.

The collector is adapted to cut a sample of tissue from an animal or plant, using the cutter. The sample can temporarily be held by the cutter such as within the sample holding section. To release the sample from the sample holding section, the plunger can be pushed from its active position so that it moves in the direction of the sample. It may be pushed into the bore of the punch more and toward the cutting edge and through the sample holding cavity so that the tissue sample is pushed off the cutter.

Although in a preferred form the punch is substantially tubular and the plunger is substantially cylindrical, it is envisaged that the punch and plunger may be of any suitable complementary shape. For example, the bore of the punch may have a square cross-section and the plunger may also have a square cross-section of a slightly smaller size so that the plunger can slide within the bore of the punch. It should be appreciated that the cutting edge of the cutter could also be of any suitable shape and size to cut a tissue sample that fits within the storage container for receiving the sample. For example, the cutting tip may be square, oval, star shaped or irregularly shaped.

In the preferred form the collector is held by a tissue sampler as will herein after be described that also holds the storage container at the time of sampling.

In one form, as shown in FIGS. 3a to 3d, the storage container 500 comprises a container body 510 having an open first end 501a and a closed second end 501b, which forms the base of the container body, although it should be appreciated that the container body will not always be oriented so that the base is at the bottom of the container body.

Figure 9:
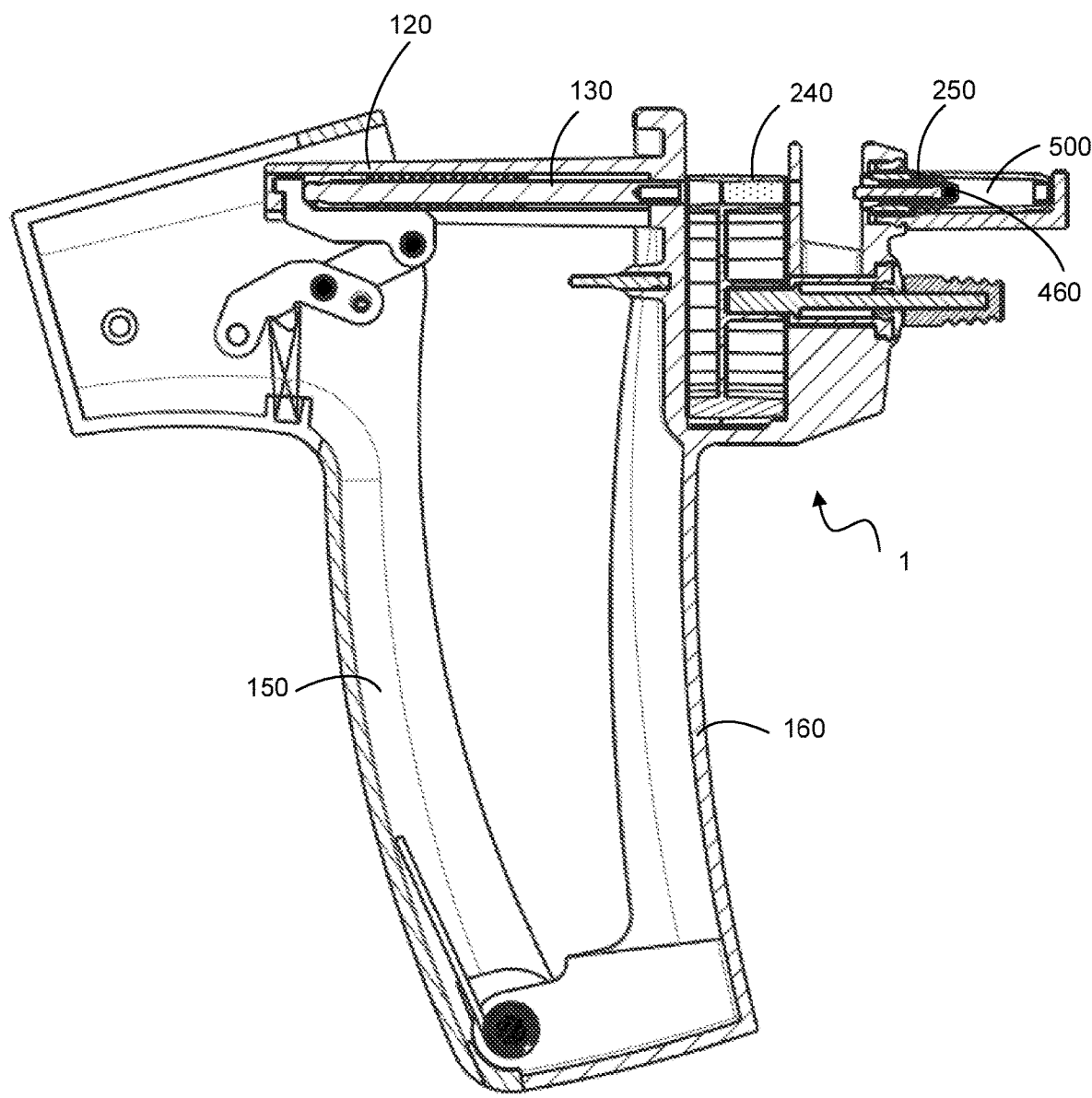
FIG. 9 is a cross-sectional side view of the tissue sampler of FIG. 6 in which the ram has been retracted through an empty chamber of the collector magazine and is returned to its rest position.
Figure 10:
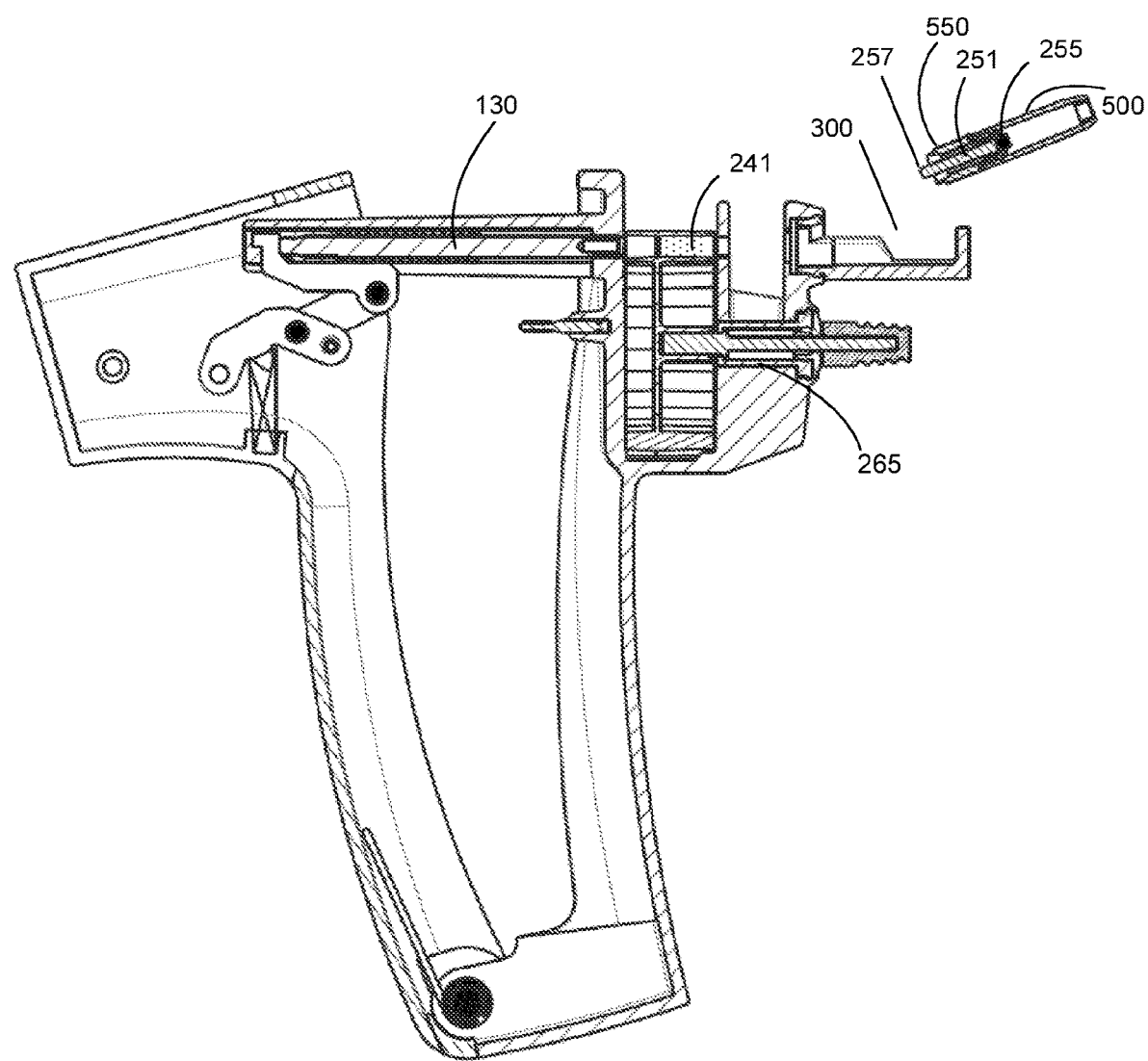
FIG. 10 is a cross-sectional side view of the tissue sampler of FIG. 6 in which the storage container containing a tissue sample and collector is being removed from the sampler.

Optionally, the base of the container body is flat and unique indicia 502, such as a bar code, QR code, matrix code, or the like is provided on the base, as shown in FIG. 9d. This machine readable code assists in processing and tracking. Alternatively or additionally, unique indicia is provided along the side of the container body. The unique indicia is used to provide information about the source of the sample that will ultimately be placed within the storage container 500. An RFID may instead or also be attached to the container.

A collector located RFID tag is useful for tracking and tamper prevention purposes. The RFID may be used at the time the sample is taken, it identifies the sample to a collector ID.

Prior, during or immediately after the sample is taken, the sample collector RFID tag can be read and stored along with a unique ID that is derived from a storage container ID and/or derived from an animal associated ID such as from an ear tag carried by the animal tested. This will ensure that at least 2 and preferably three individual identifiers (eg numbers) are locked to a sample taken. One from the collector RFID tag, and one from said animal associated ID and preferably from said container. These linked numbers are stored at sampling time in a database. The aim is to make it tamper resistant and limit the options to substitute samples. The container's (when used and when carrying an ID) and the collector's ID may be read during the lab processing and again checked to the database. The methods to read/transfer information from the container, collectors and ear tags at sampling would be existing technologies of reader and an intended reader within the sampler if possible. The data collected at the laboratory from the RFID devices would be unique identifier with which information derived from sample testing can be associated.

In one form, the container body 510 comprises a tissue sample chamber 503 at its base to receive a tissue sample. A preservative 505 may be provided in the tissue chamber.

Preferably, the outer surface of the container body comprises anti-rotation means 504 located at or near the base of the container body, as shown in FIGS. 3a to 3d. The anti-rotation means comprise one or more recesses and/or projections adapted to prevent the container body from rotating within a cell of a holding rack, as will be described later in this specification.

Optionally, the storage container comprises a cap that attaches to the open first end of the container body to seal the container body. Alternatively, the cap may have an aperture formed therein through which a tissue sample can pass to be placed in the container body. In this form, the cap is attached to the container body, but does not fully seal the container body.

Preferably, the container body comprises a threaded region at or near its first end that meshes with a threaded region of the cap to allow the cap to be screwed onto and off the storage container body. Alternatively, the cap is attached to the open end of the container body with a snug fit. In yet another form, the cap comprises a lip on its inner surface that nests within a channel that surrounds the outer surface of the container body near the open end of the container body. As will be appreciated, the cap may be attached to the container body in any other suitable arrangement and these are just some examples that could be used. A threaded relationship is preferred because it assists in cap removal.

In one form, as shown in FIGS. 6a to 6e, the storage container 500 comprises a cap 550 that is screwed onto a threaded region 506 of the container body 510, as described above. In particular, the cap comprises a threaded shaft 551 that is adapted to engage with a threaded interior region 506 of the storage container 500 so that a first end of the shaft projects toward the base 501b of the body. Alternatively, the shaft may have a threaded bore that is adapted to engage with a threaded exterior region of the container body so that a first end of the shaft projects toward the end of the container body. A collar 552 extends from the opposing second end of the threaded shaft. The collar 552 comprises an outwardly projecting annular flange 553 and a guide wall 554 that extends from the periphery of the flange 553 in a direction away from the shaft 551 to form a substantially cylindrical wall. Preferably, an outer surface of the guide wall is contoured or textured to provide a knurled cap.

A centrally located recess 555 is provided within the collar 552 and between the guide wall. The recess may be specially shaped for engagement with a correspondingly shaped cap-release tool to remove the cap from the container body. For example, the recess 555 may have a tool-engageable edge 559 that provides the recess with a cruciform shape, star shape, hex shape, square shape, oval shape, or any other regular or irregular shape that corresponds to the shape of a tool for inserting into the recess and turning the cap to unscrew the cap from the container body. However, it is preferred that the outer surface of the guide wall is shaped to correspond with the shape of a tool, or to at least provide a gripping region, for gripping the outer wall and turning the cap to decap the storage container.

The recess 555 aligns with a passage 556 that is centrally located through the cap. The cap also comprises a breakable seal 557, which may be in the form of a membrane, or the like, that extends laterally across the cap. The seal may be formed integrally with the collar and shaft of the cap so that the entire cap is made as one part. Preferably, the seal is located at or near a first end of the shaft, but in other forms, the seal may be located within the collar of the cap or in any other suitable location. The seal 557 may be of any suitable material, such as polypropylene, rubber, polyethylene, or the like. When the cap 550 is attached to the body of a container body 510 so that the first end of the shaft projects into the body, the seal 557 extends across the body to seal the first end 501a of the container body. Preferably, the cap 550 also comprises a second seal 558, such as an o-ring, that fits over the outside of the threaded shaft 551 and abuts the collar 552 of the cap. In this form, when the cap is attached to the body of a storage container, the second seal is positioned between the first end 501a of the body and the collar 552 of the cap 550 to seal the connection between the cap and the body. In this arrangement, the cap can be screwed onto a sterile body to hermetically seal the containment region in the body. The interior of the body can remain sterile until the seal is broken and a tissue sample is placed in the container body.

In the preferred form the cap and the container body are engaged to each other in a tamper evident manner. This allow for detection of the removal of the cap from the container body. Preferably the tamper evident manner provides some visual evidence of tampering. For example, connecting tabs may be provided between the collar and an attachment ring of the cap that is securely attached to the tube. In this form, if the cap is twisted away from the attachment ring (such as by unscrewing the cap from the body), the connecting tabs break to indicate that the storage container has been tampered with. A shrink wrap over the container cap interface may be used as a tamper evident indicator. A sticker may be used that will pull apart when the cap and container are separated. A frangible ring or the like could be used also.

In a preferred embodiment connecting tabs 701 are secured at one end to a collar 705 on the cap or to the cap itself. The connecting tabs 701 are also secured in a frangible manner at another end to an attachment ring 703. The container 500 comprises complementary engaging features 702 which complement the shape of the connecting tabs 701. In one embodiment a ring of engaging features 702 are spaced about the periphery of the container 500. The connecting tabs 701 are configured to fit between the spaces of the adjacent engaging features 702. The attachment ring 703 is designed to not be able to pass over the top of the engaging features 702. As such when the container 500 is locked on the cap 550 the engaging features 702 and the connecting tabs 701 engage with each other to prevent any twisting motion, whilst the attachment ring 703 prevents any translational movement of the cap from the container 500. The cap 550 is secured to the container 500 during production or manufacture. In one embodiment the attachment ring 703 is allowed to slide overtop of the engaging features 702 in one direction (towards each other), but not in another direction (away from each other).

Figure 17:
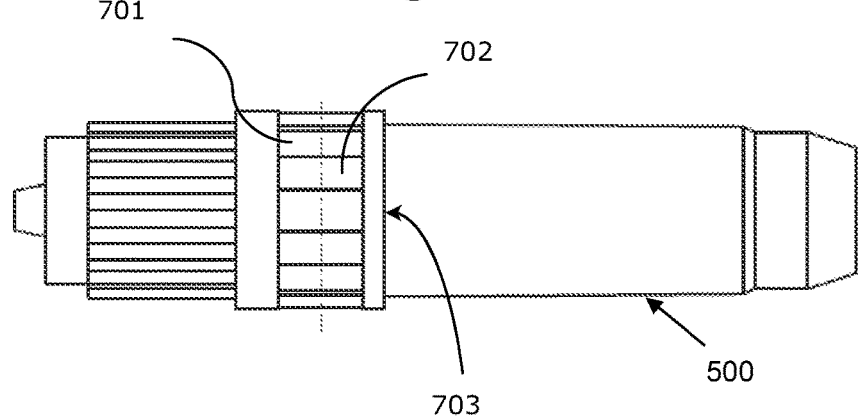
FIG. 17 is a side view of FIG. 16 in a collapsed condition.
Figure 18:
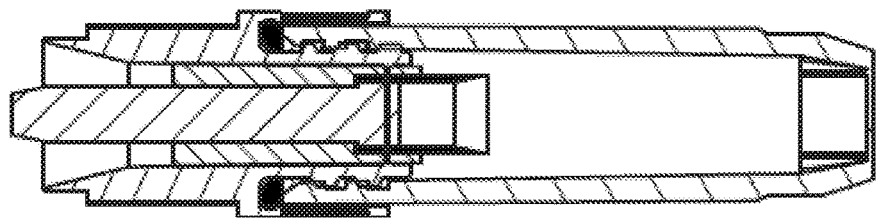
FIG. 18 is a side cross section of FIG. 17.
Figure 19:
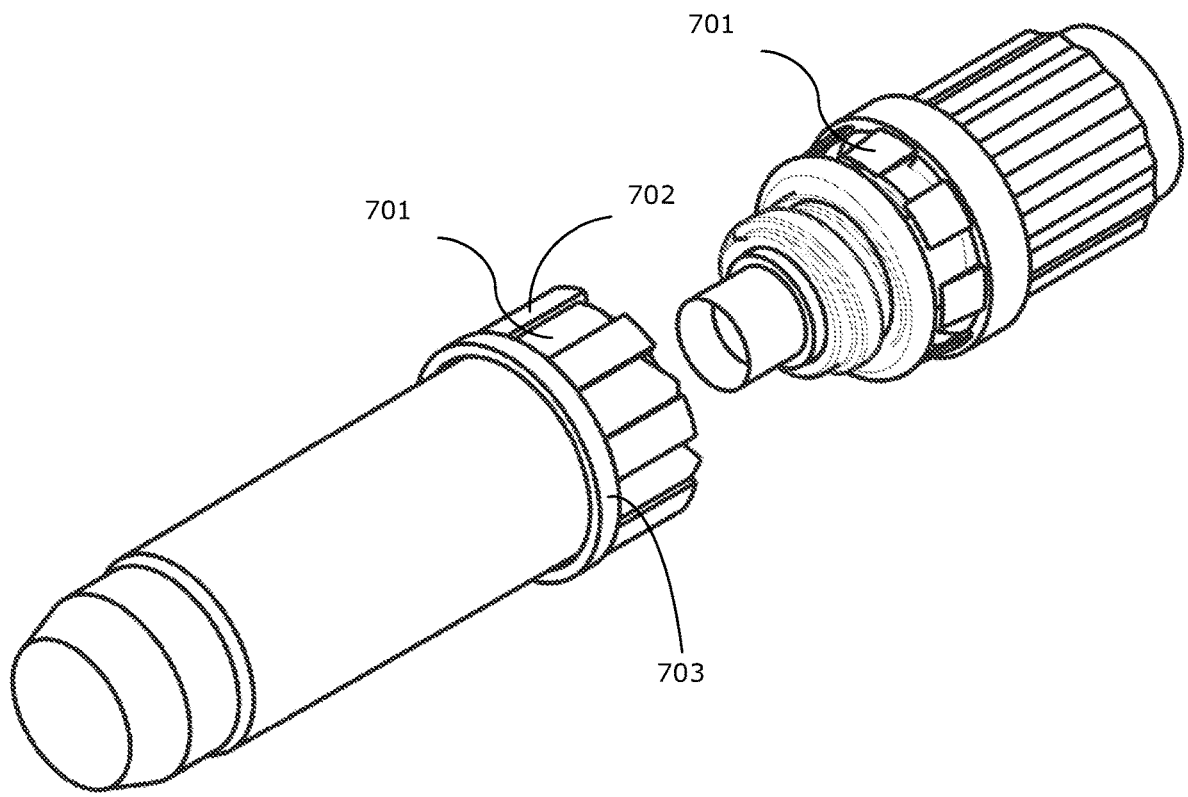
FIG. 19 is a perspective view of a tamperproof collector and associated storage container with the tamperproof seal broken.
Figure 20:
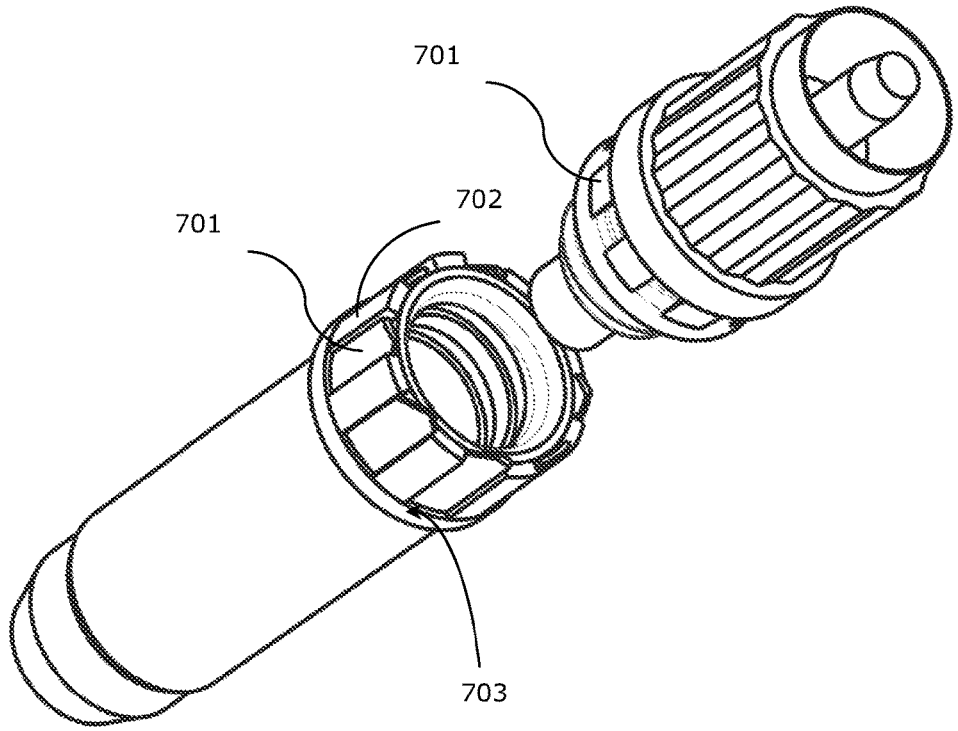
FIG. 20 is another perspective view of FIG. 19.
Figure 21:
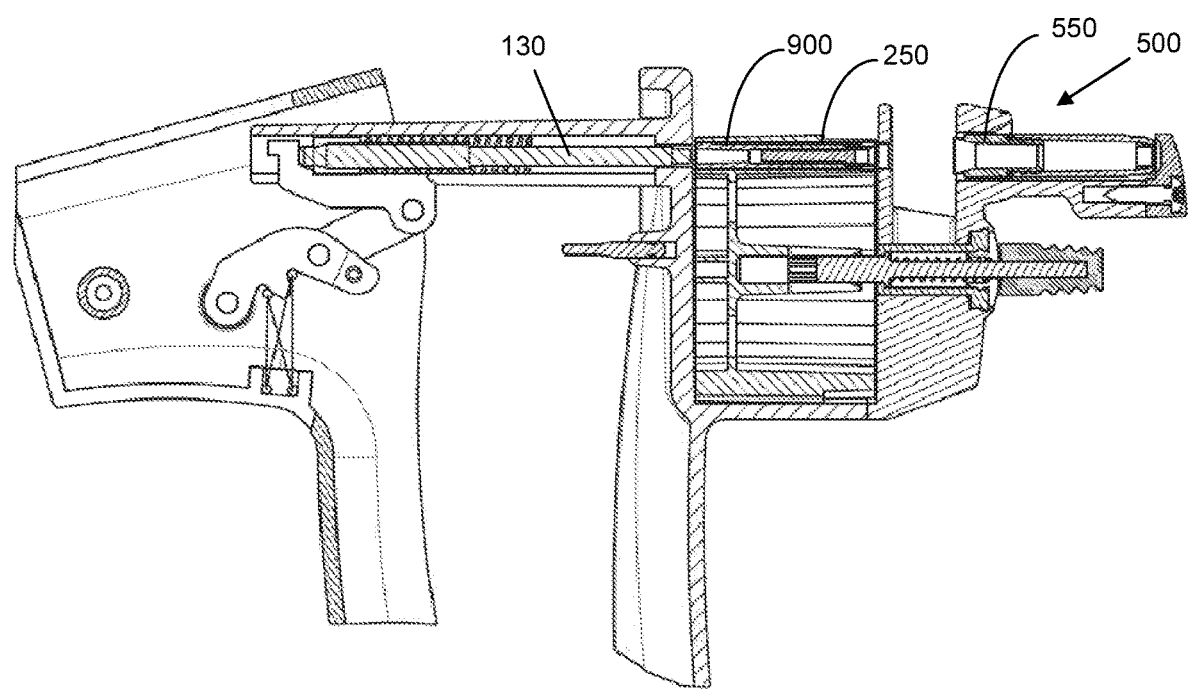
FIG. 21 is a sectional view of a sampler showing a variation where a disposable shield is utilised to prevent the ram from contacting the tissue surfaces and thereby avoid any cross contamination.
Figure 22A:
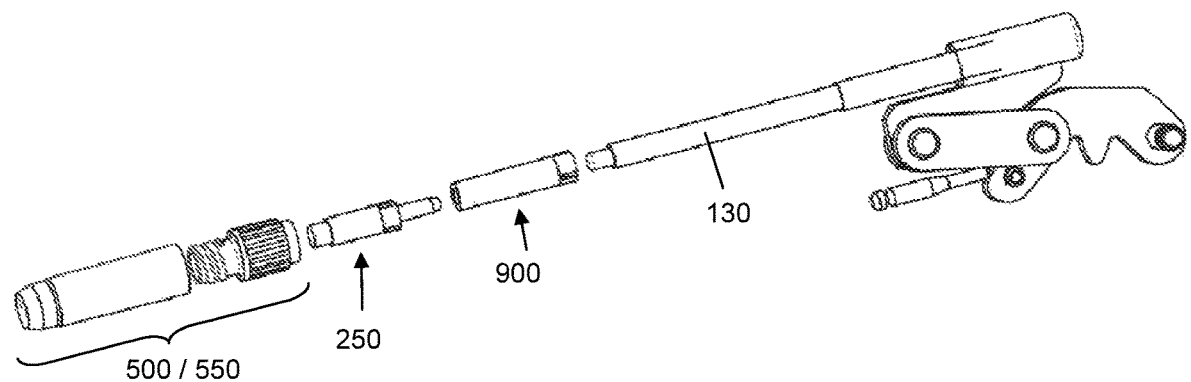
FIG. 22a is an exploded perspective view of part of the sampler and the shield together with the collector and storage container.
Figure 22B:
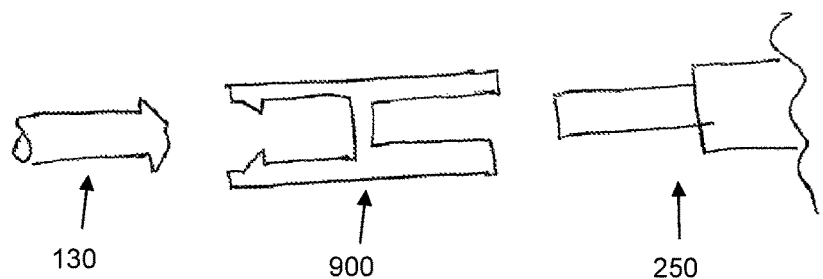
FIG. 22b is a partial sectional view of the ram, shield and collector.
Figure 23:
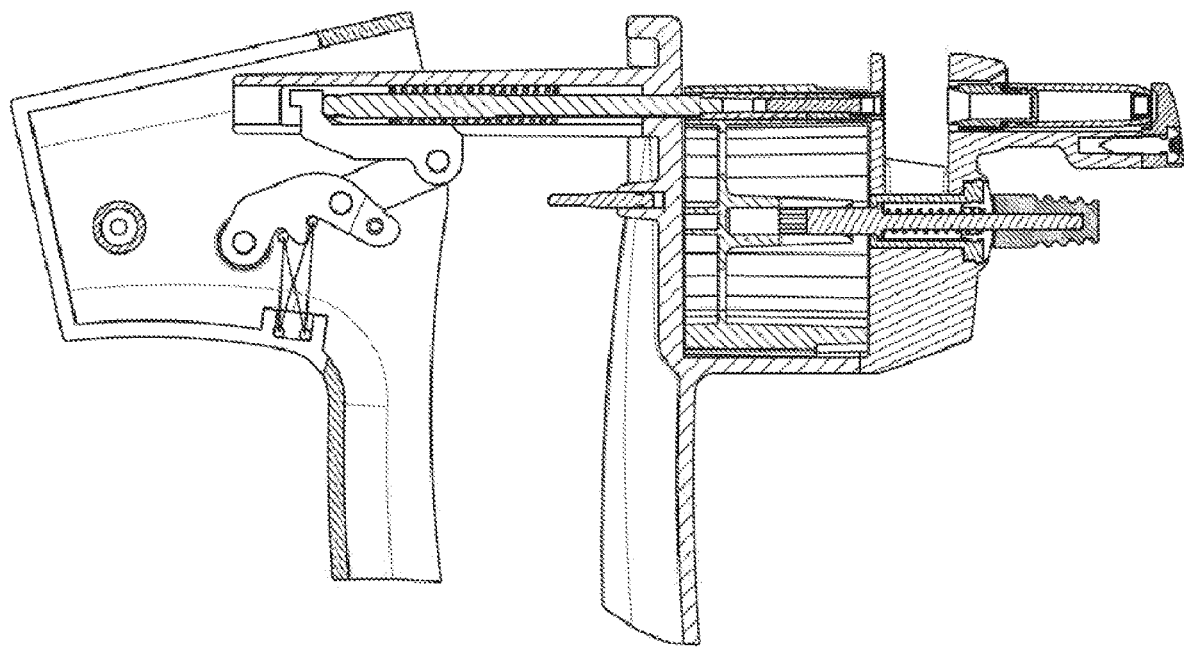
FIG. 23 is a view of the collector of FIG. 21 wherein the ram has moved to engage with a shield for the purposes of driving a collector from the magazine.
Figure 24:
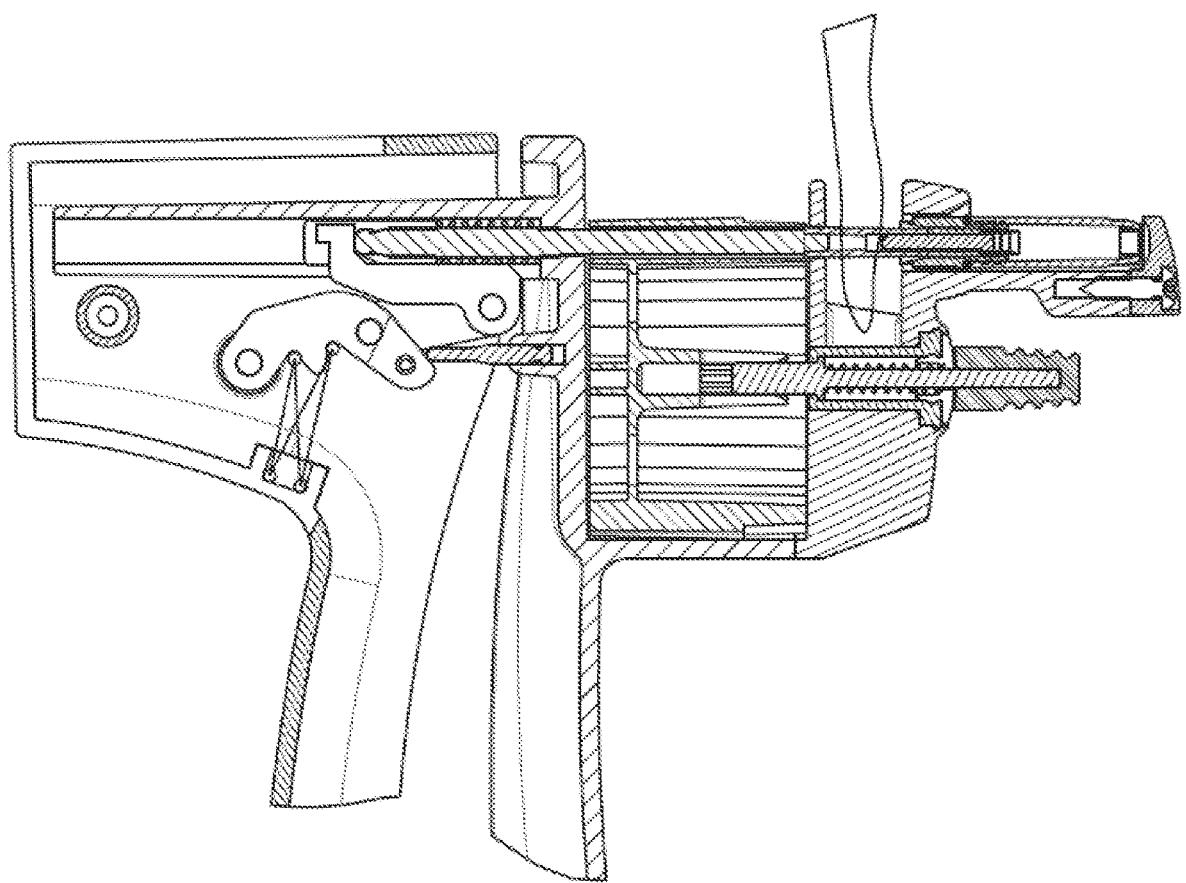
FIG. 24 shows the ram in a more advanced position having pushed the collector to engage with the storage container, the shield having penetrated into the animal tissue.
Figure 25:
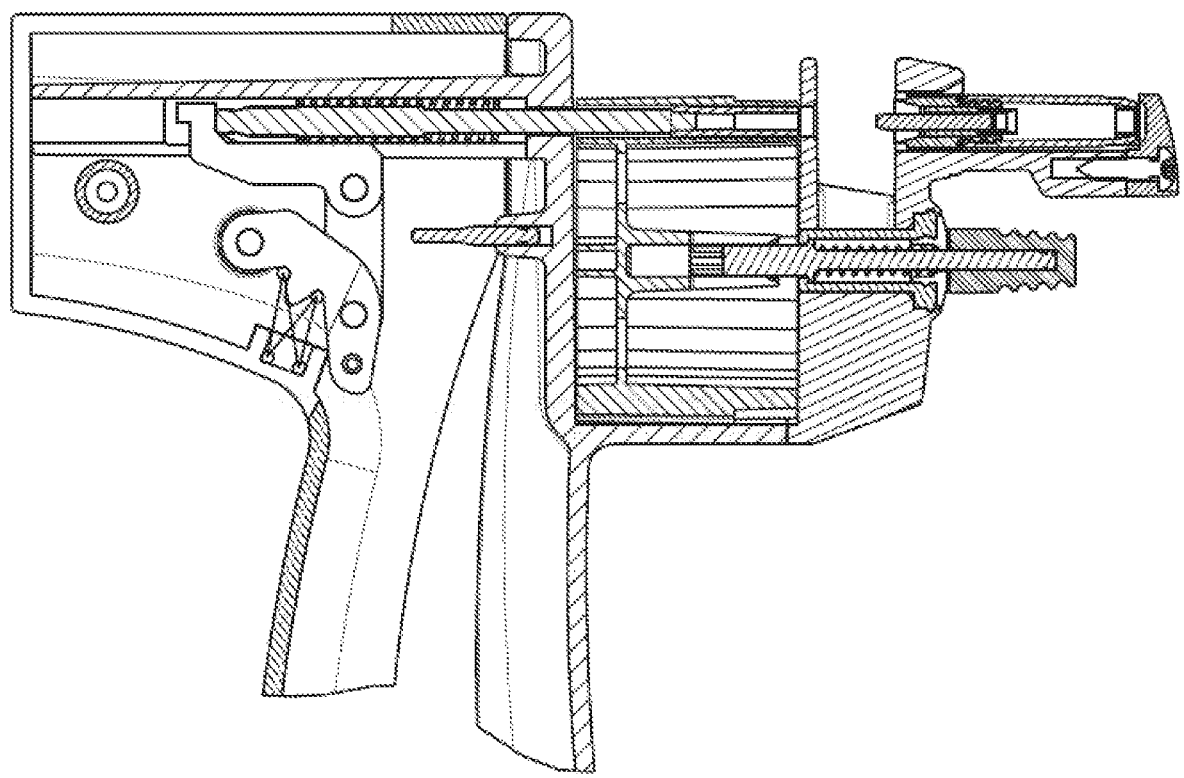
FIG. 25 shows a retraction of the ram taking with it the shield for return of the shield to the magazine having left the sample collector associated with the storage container.
Figure 26:
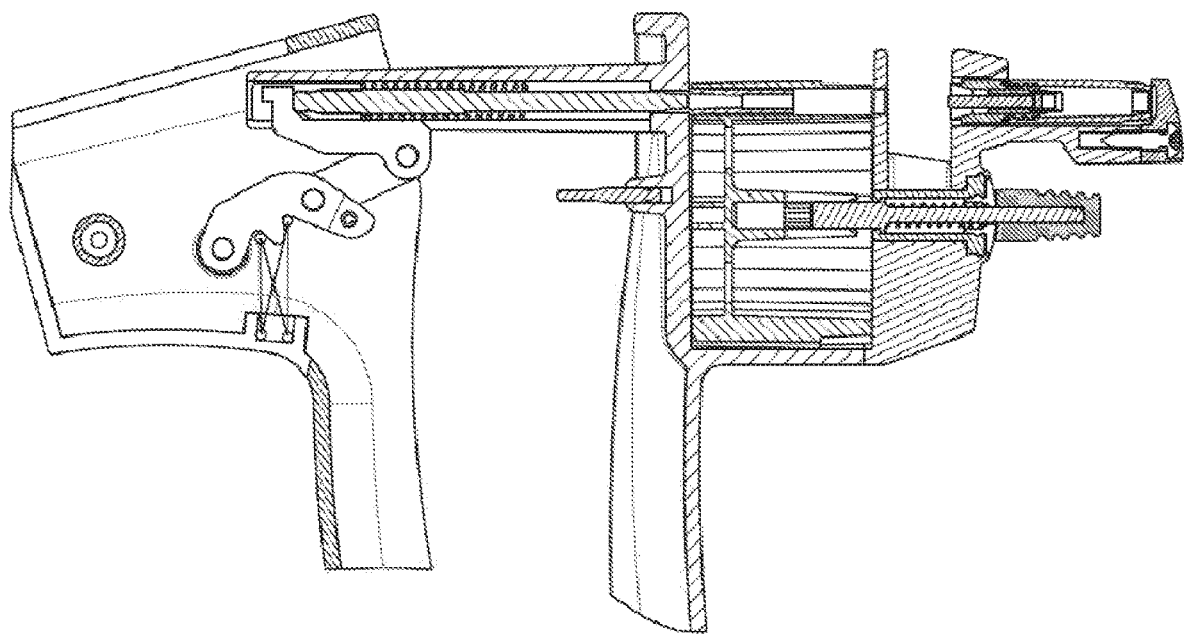
FIG. 26 shows the ram having retracted to its withdrawn position and the shield located back with the magazine.

The cap 550 and the storage container 500 are shown threadingly engaged in FIGS. 17 and 18. To remove the cap 550, the cap must be rotationally turned and the connecting tabs 701 will frangibly disconnect from either the attachment ring 703 or the collar 705. This frangible disconnection is a visual cue that allows a user to identify whether the storage container 500 has been opened. FIGS. 19 and 20 show a perspective view of a frangibly disconnected storage container 500 and cap 550. Once a frangible disconnection has occurred, the cap 500 can be removed from the container.

Figure 4:
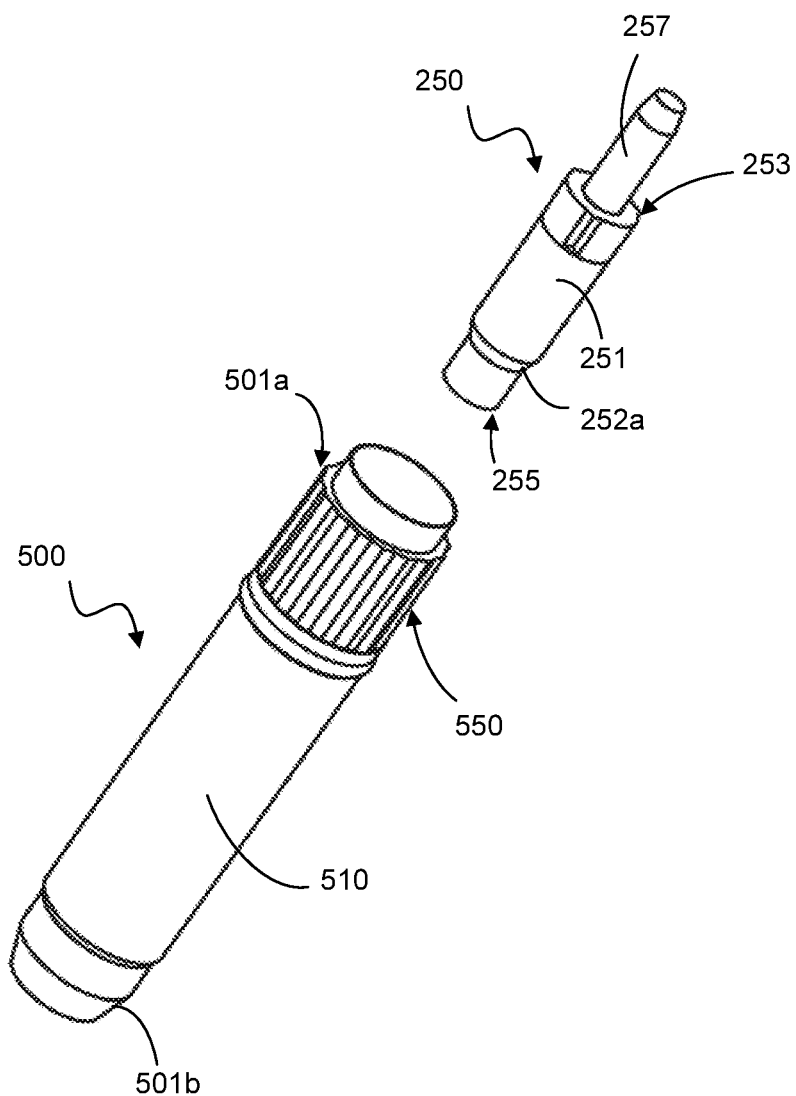
FIG. 4 is a perspective view of one form of the collector before being inserted into a storage container.

The storage container, when used, and collector are aligned at the time of sampling as shown in FIG. 4. They are separated prior to sampling so that part of the item from which the sample is to be removed can be located there between.

As will now be described, the collector and the storage container may be so held for sampling purposes by a sampler. The sampler is described in our co-pending international application PCT/NZ2014/000106 which by way of cross reference is hereby incorporated. Pneumatically or electrically operated samplers or other are also envisaged as being adaptable for use with the present invention.

Figure 5:
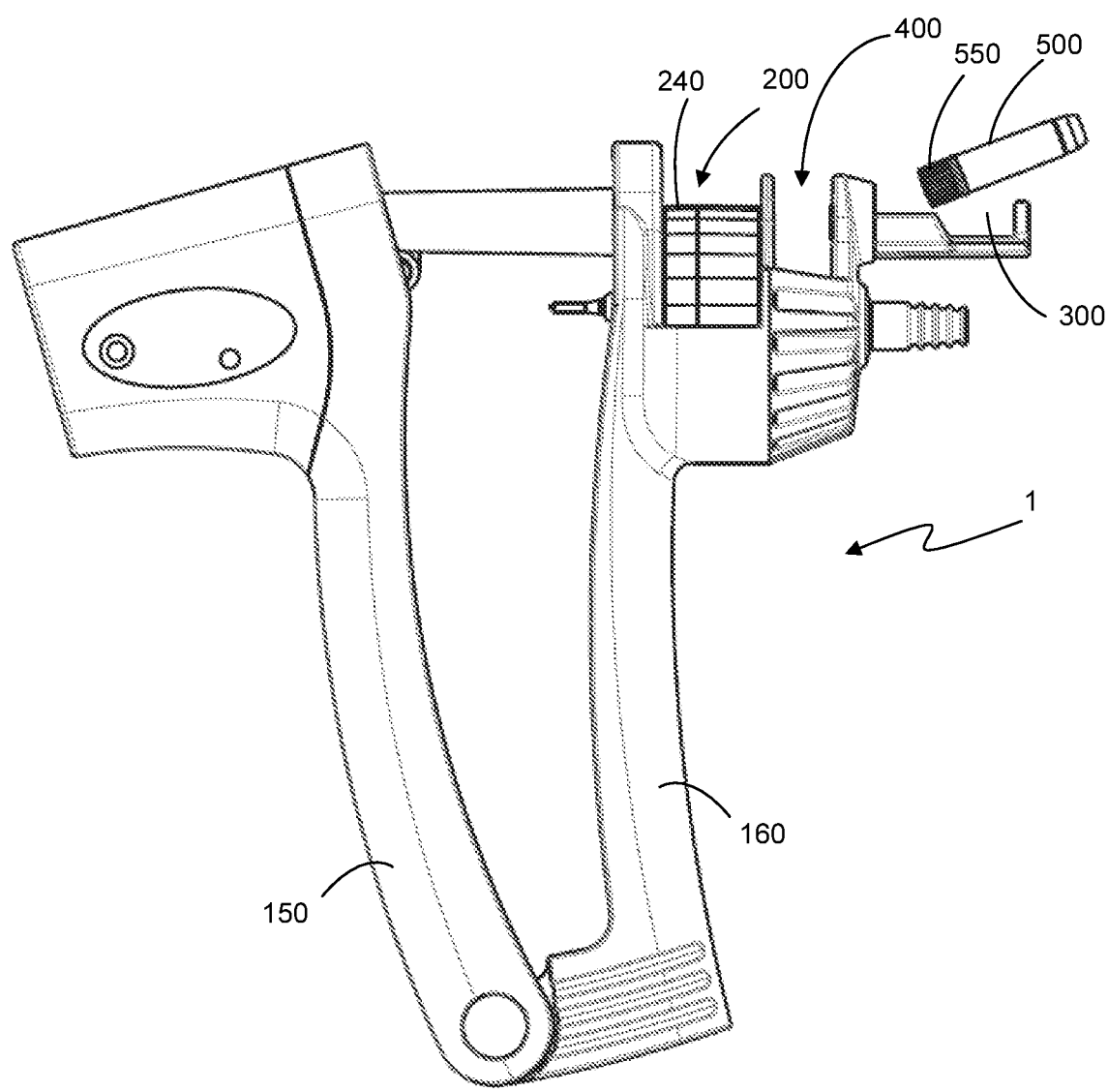
FIG. 5 is a side view of one form of tissue sampler in which a storage container is about to be placed into the tissue sampler.
Figure 5A:
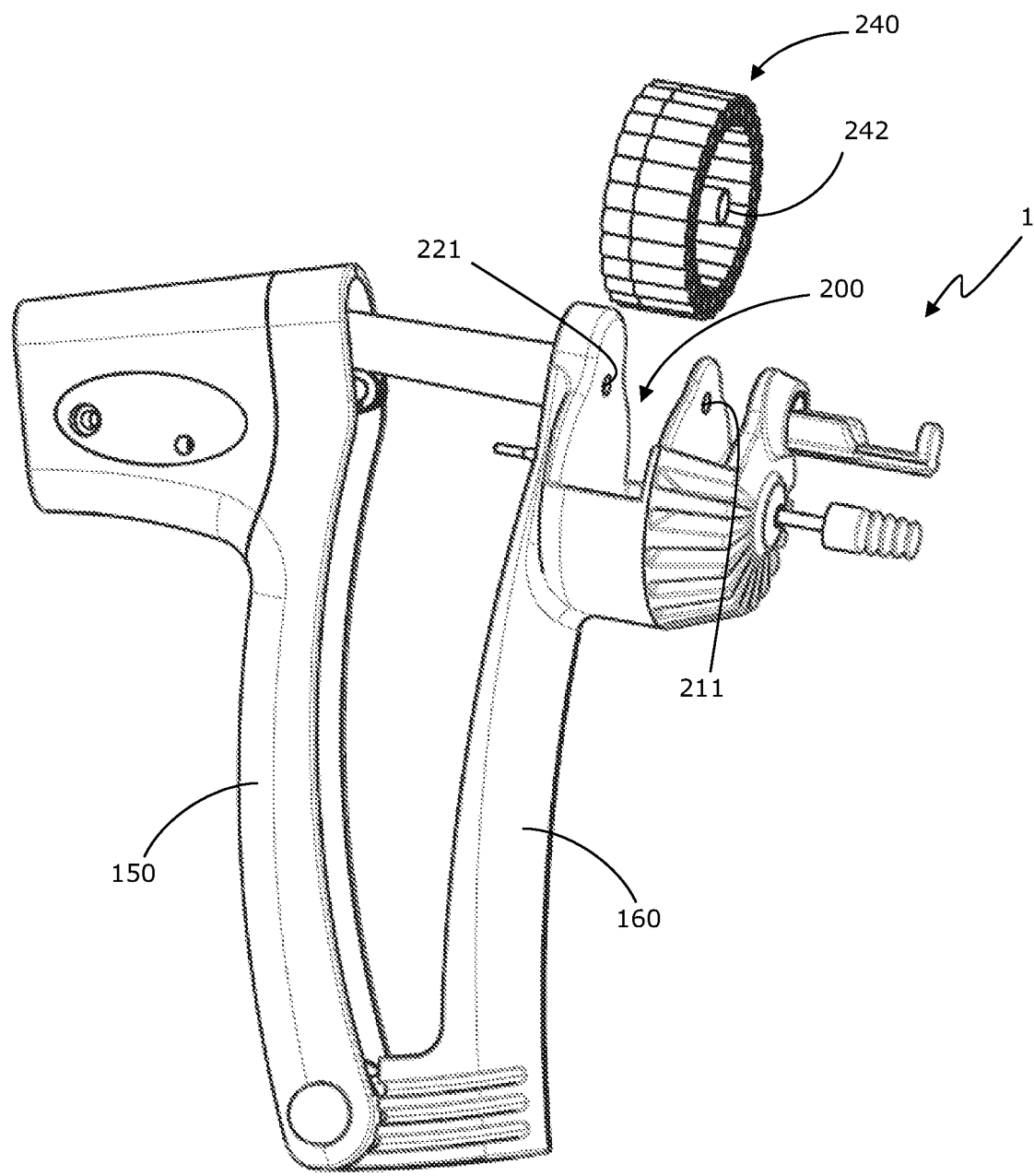
FIG. 5a is a perspective view of the tissue sampler with a collector magazine about to be placed into the magazine housing of the tissue sampler.
Figure 6:
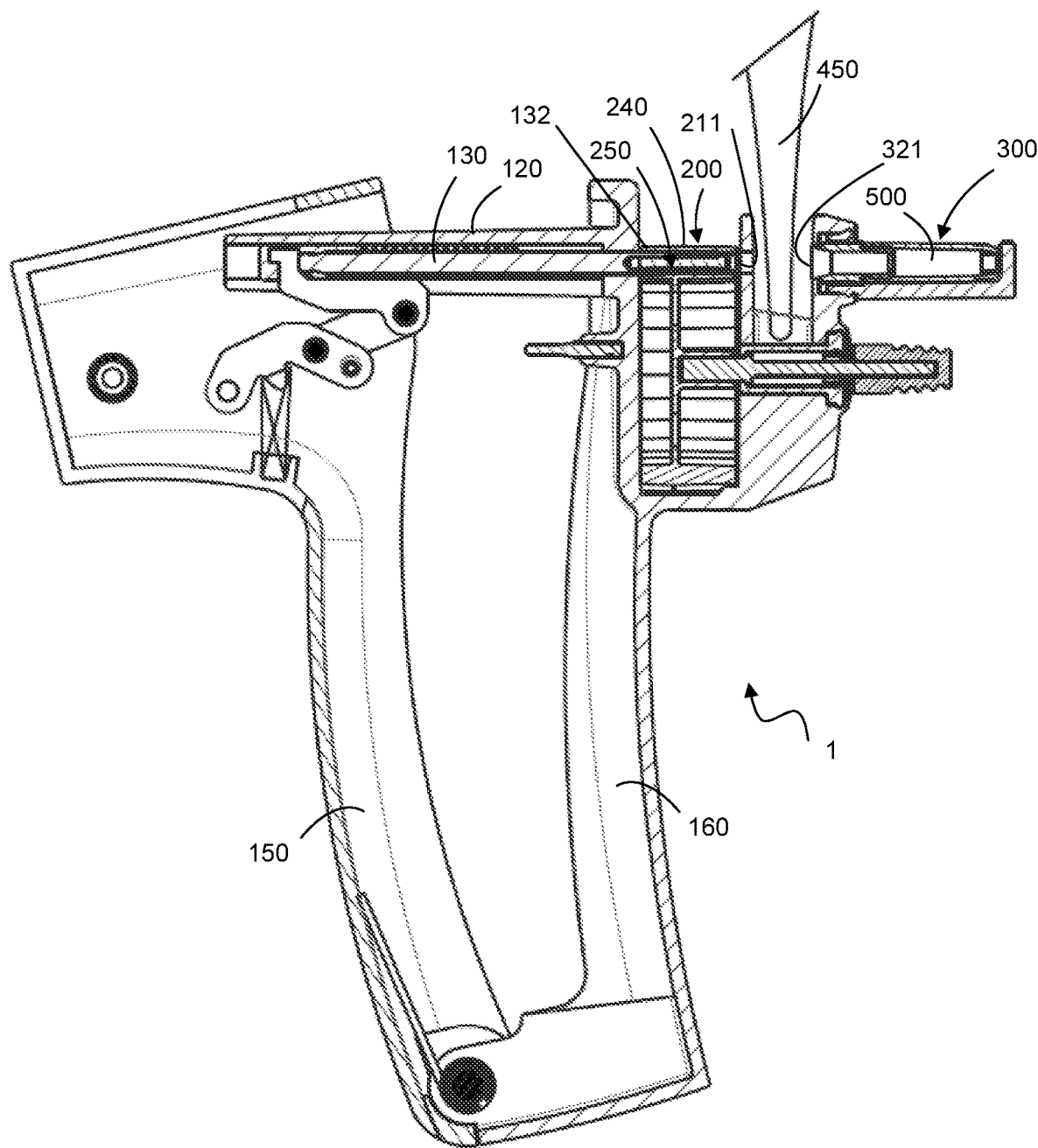
FIG. 6 is a cross-sectional side view of the tissue sampler of FIG. 5 in which an animal's ear is located in the cutting region.
Figure 6A:
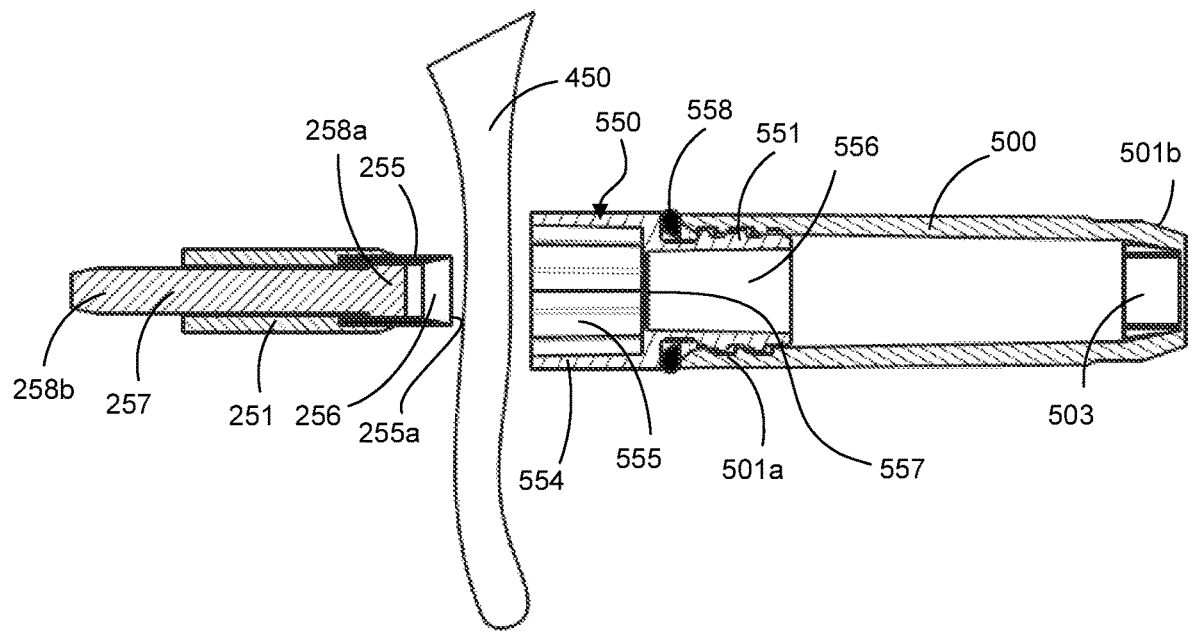
FIG. 6a is a cross-sectional side view of one form of collector before taking a tissue sample from an animal's ear and placing it into a storage container.
Figure 6B:
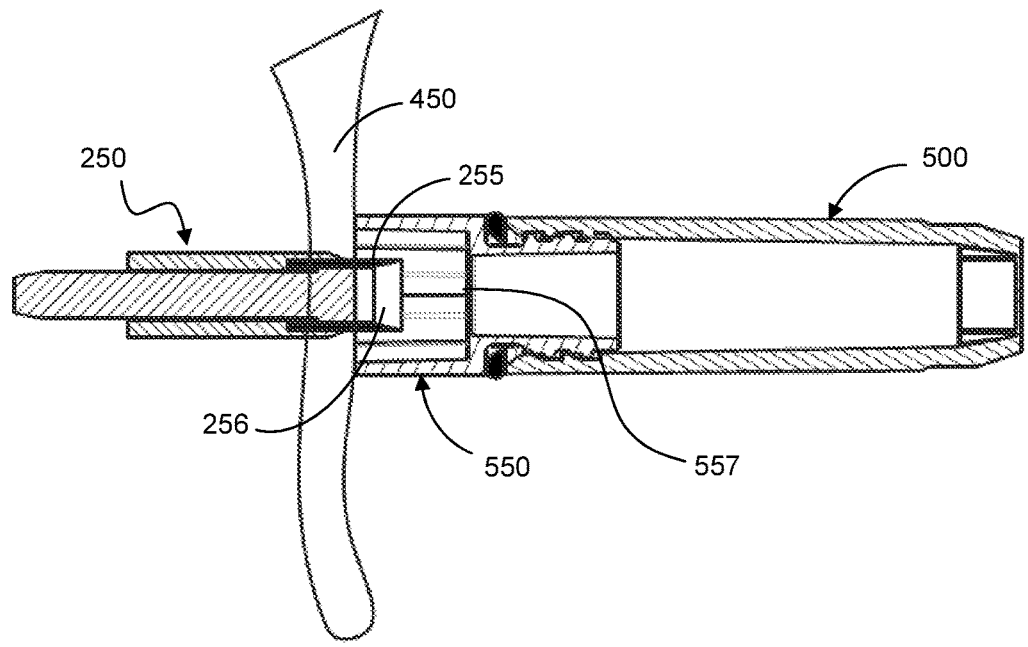
FIG. 6b is a cross-sectional side view of the collector of FIG. 6a when cutting a tissue sample from the animal's ear.
Figure 6C:
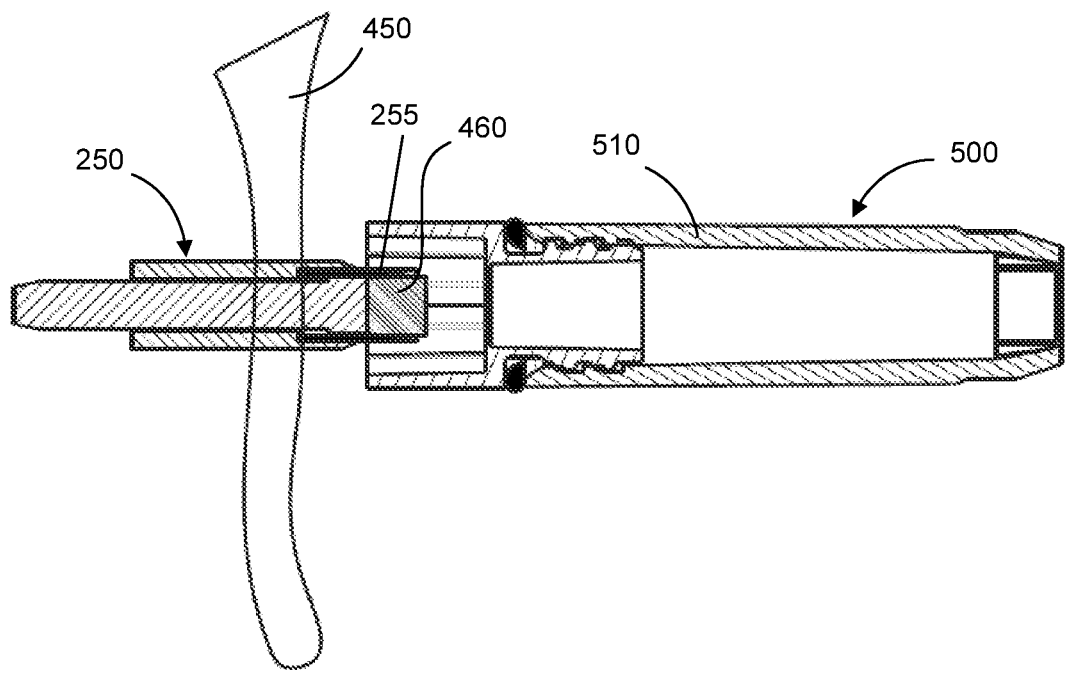
FIG. 6c is a cross-sectional side view of the collector of FIG. 6a after a tissue sample has been cut.
Figure 6D:
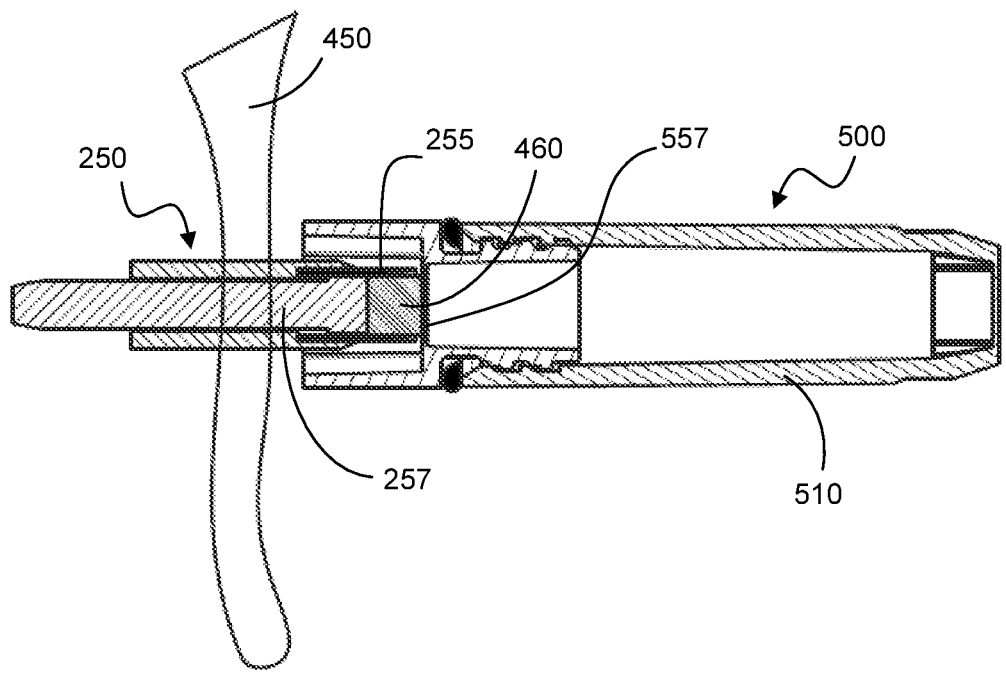
FIG. 6d is a cross-sectional side view of the collector of FIG. 6a pressing against a membrane in the cap of the storage container.
Figure 6E:
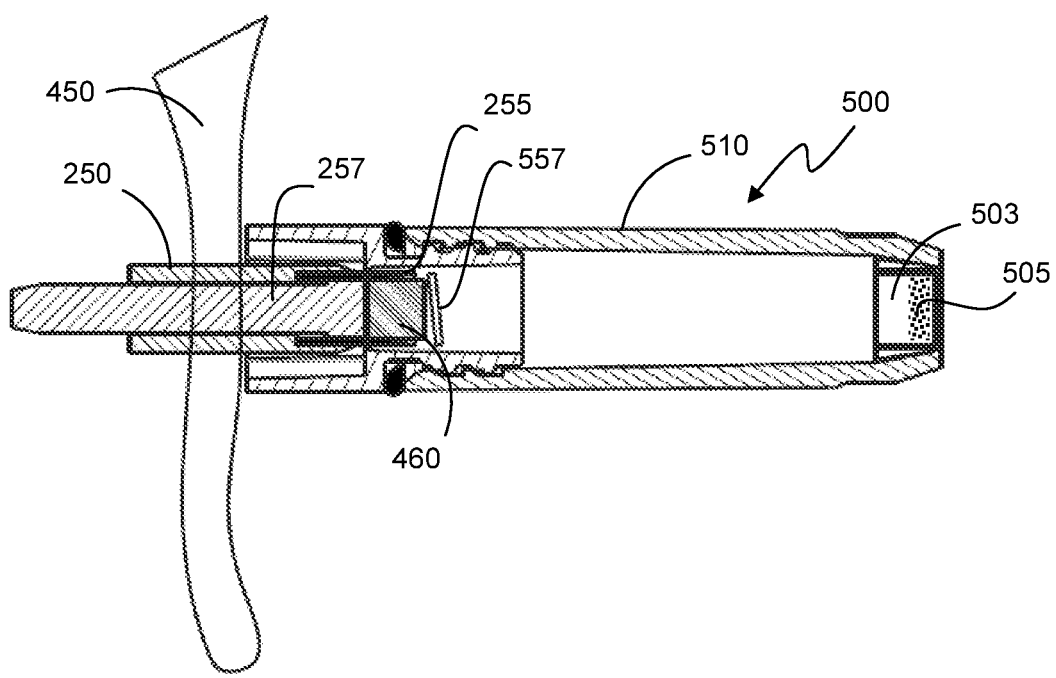
FIG. 6e is a cross-sectional side view of the collector of FIG. 6a after the membrane has been broken.
Figure 7:
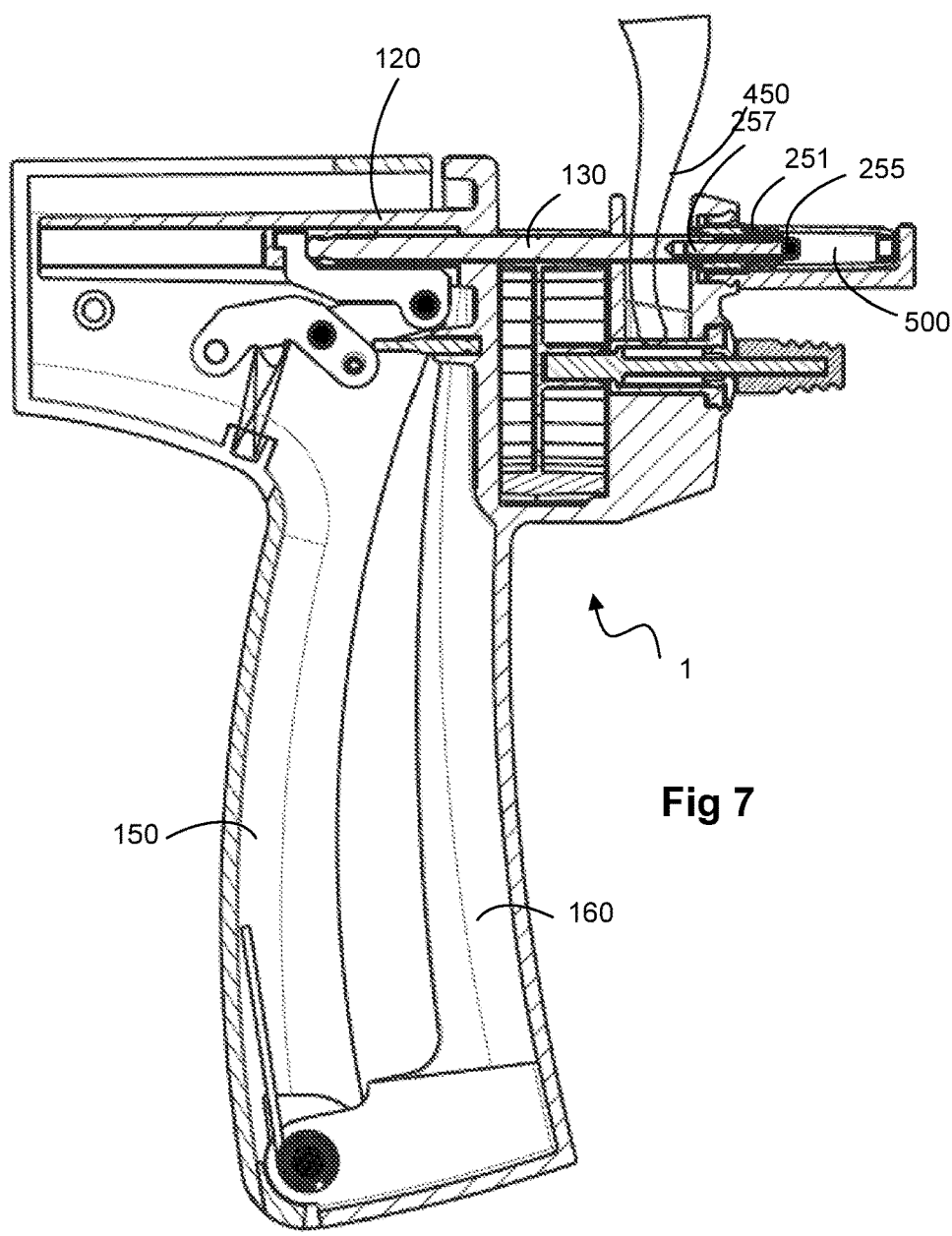
FIG. 7 is a cross-sectional side view of the tissue sampler of FIG. 6 in which a tissue sample has been cut from the animal's ear.
Figure 7A:
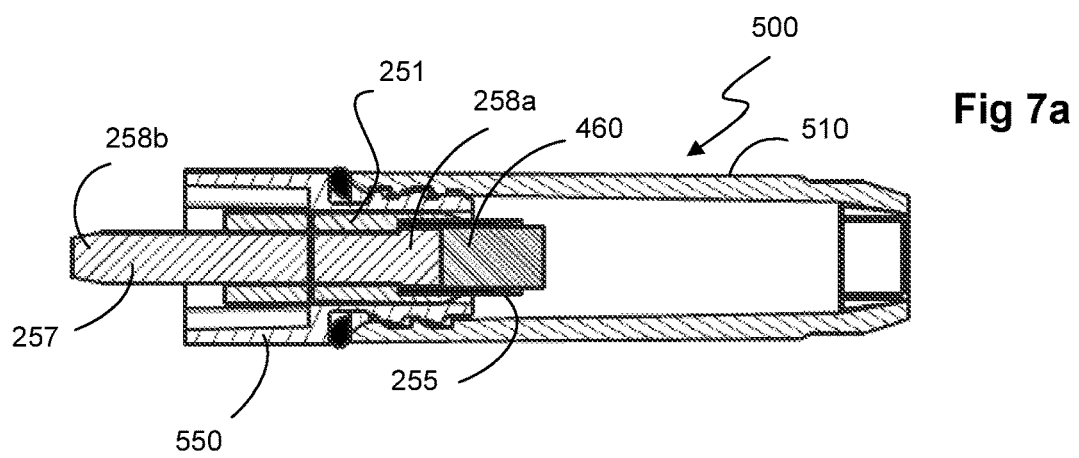
FIG. 7a is a cross-sectional side view of the collector of FIG. 6a in which it is plugging the first end of the storage container.
Figure 8:
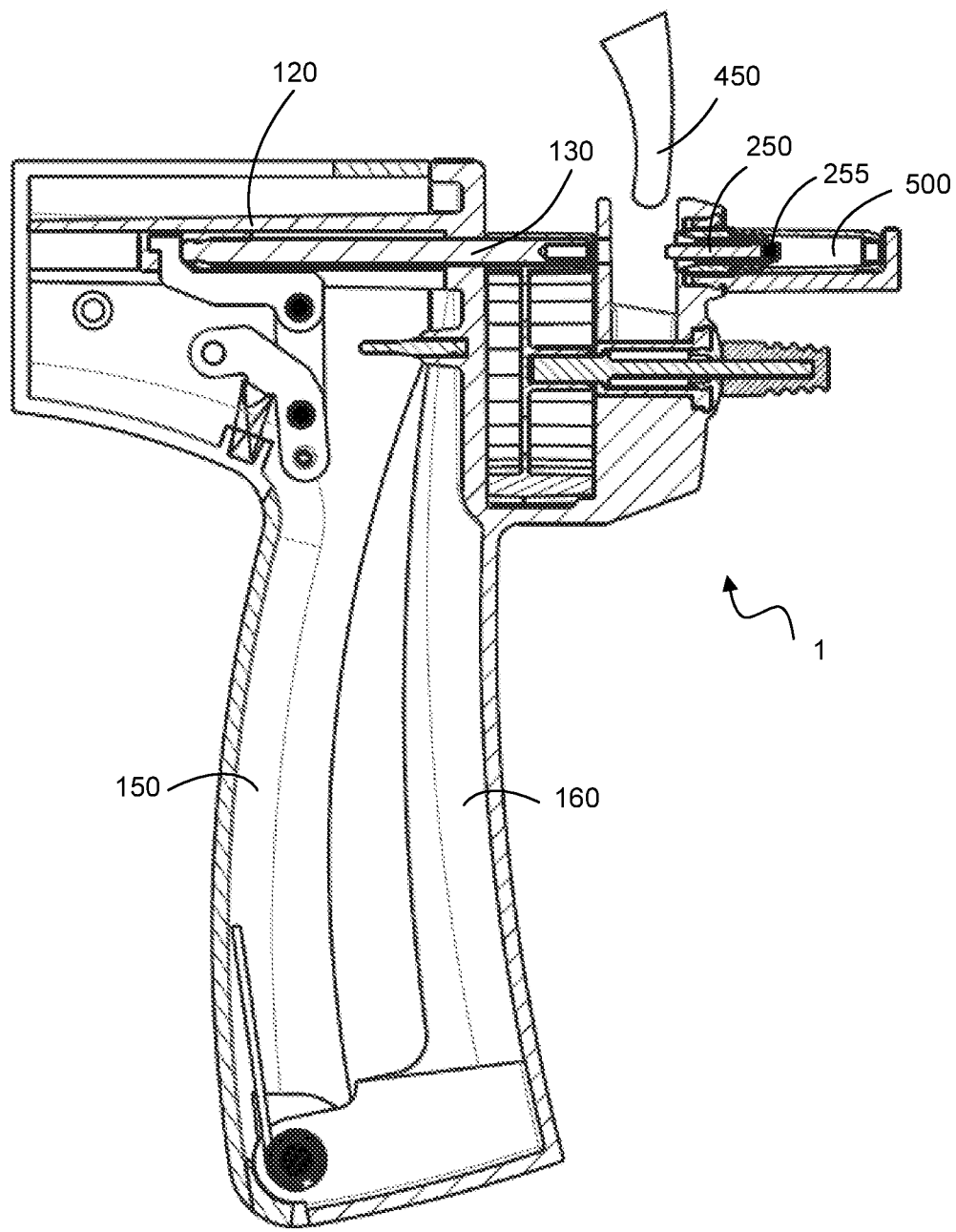
FIG. 8 is a cross-sectional side view of the tissue sampler of FIG. 6 in which the animal's ear is removed from the cutting region and the collector has plugged the storage container.

The storage container is dimensioned to fit within the storage container holder 300 of the tissue sampler 1 as shown in FIGS. 5 and 6 and to receive a collector through the first end of the storage container, as indicated in FIG. 4.

When a tissue sample is to be taken, a storage container 500 is placed in the container holder 300 so that its first end 501 faces toward the cutting region 400, as shown in FIG. 5.

A plurality of collectors 250 may be positioned within a magazine housing 200 loaded into the tissue sampler. The magazine can sequentially present each collector for sampling. This is achieved by aligning the collectors individually with an actuator such as a ram 130 of the sampler 1.

Figure 11:
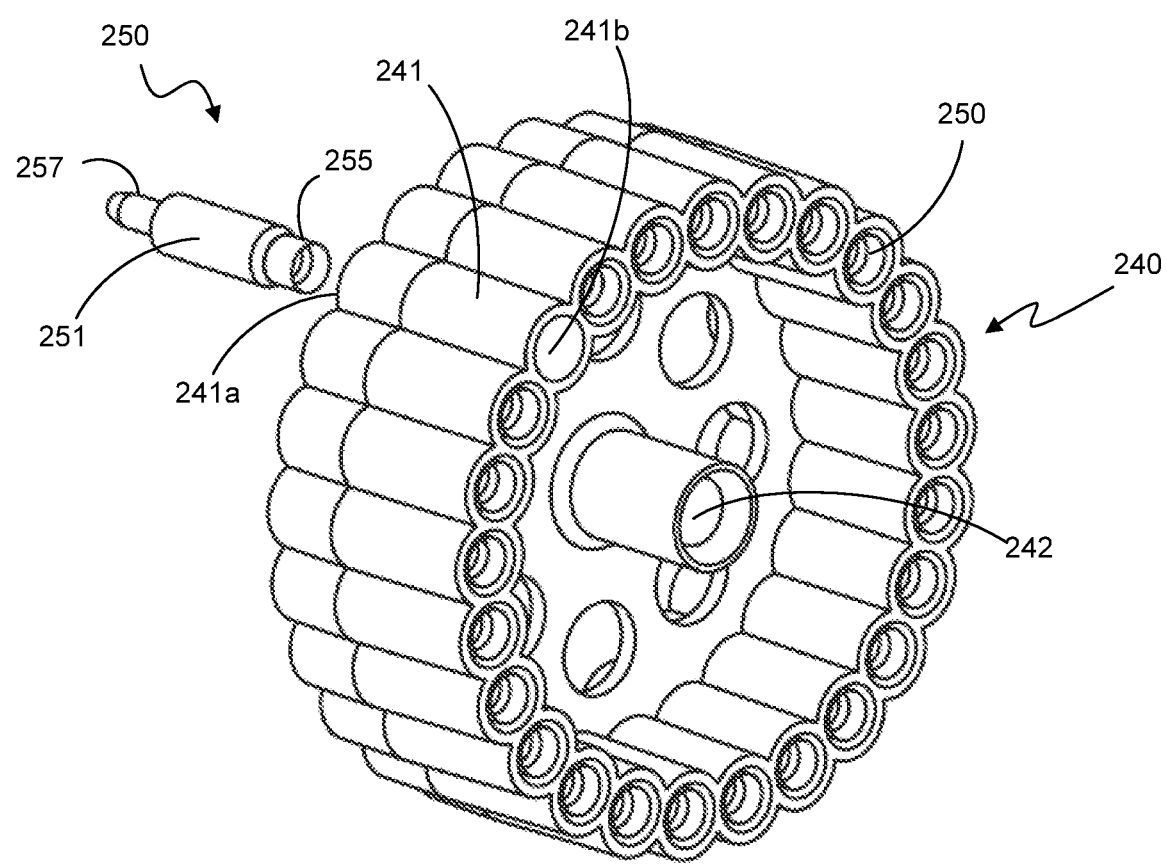
FIG. 11 is a perspective view of a collector magazine.

As shown in FIG. 11, the magazine housing 200 is sized to receive a magazine 240 comprising a plurality of chambers 241, each chamber being adapted to hold a collector 250 therein and having open first and second opposing ends 241a, 241b. The magazine, is preferably in the form of a cylinder having a centrally located axle or bore 242 that extends through or into the magazine. The chambers are positioned concentrically around the bore and preferably near the circumference of the magazine. Preferably, at least a portion of the chambers in the magazine 240 is of a transparent material, so that the presence of a collector in any of the chambers can be identified. In the embodiment shown in FIG. 11, the magazine comprises 25 chambers, although the magazine may have any suitable number of chambers. In the preferred form the magazine can rotate to index collectors for actuation. In other forms the magazine may translate instead.

The second end of the collector aligns the ram 130 and the cutting edge 255a of the cutter 255 aligns with a cutting region aperture 211 of the sampler, as shown in FIG. 6.

The storage container holder 300 of the tissue sampler is adapted to hold a storage container 500 therein.

As shown in FIG. 5 the cutting region 400 comprises a space in which tissue 450 from a sample specimen can be positioned. In FIG. 6, an animal's ear 450 is schematically shown positioned within the cutting region. The ear, or other item, is kept in the cutting region as a tissue sample is cut from the ear.

A ram 130 is positioned within the ram housing 120 of the sampler. The ram forms part of an actuating means, which also comprises a trigger 150 operably connected to the ram 130. A guiding recess 132 is formed in the first end of the ram and is shaped to correspond with the second end 258b of the plunger, which projects from the punch. The guiding recess 132 is dimensioned so that the projecting portion of the plunger can fit within the recess and so that the first end of the ram 121a can abut the pushing end 252b of the punch. This prevents the ram actuating the plunger during sampling, only driving the collector through the sample specimen by pushing on the punch.

The ram 130 is adapted to slide back and forth within the ram housing 120 as the trigger 150 is engaged and disengaged.

To cut a tissue sample, a user may use the sampler as herein described. They may insert a storage container 500 into the holder 300 so that a portion of the storage container is pushed into the sampler receiving aperture 321 so that the first end of the storage container projects slightly from the sample receiving aperture 321 and into the cutting region, as shown in FIG. 6. The magazine 240 is orientated so that the cutting edge of a punch 251 of the active collector 250 is aligned with the cutting region aperture 211 and the second end of the plunger 257 is aligned with the ram receiving aperture 221. As will be appreciated, the magazine can be placed into the tissue sampler before or after the storage container is placed in the tissue sampler.

The user then holds the handle of the tissue sampler and positions the sampler so that tissue 450 to be sampled (such as of an animal's ear) is located in the cutting region 400, as shown in FIG. 6. The user squeezes the trigger 150 toward the gripping member 160 to move the trigger from the disengaged position to the engaged position.

The ram moves through the ram receiving aperture and pushes against an active collector. The ram continues pushing to push the collector out of the chamber of the magazine, through the cutting region aperture, into the cutting region, and toward the storage container.

As the ram pushes the collector through the cutting region, the cutting end of the punch pushes the animal's ear (or other tissue) against the first end of the storage cap and the first wall of the cutting region. The cutting edge of the punch is then pushed through the ear or other tissue to cut a sample plug from the tissue. At cutting the punch and cap act as a punch and die. The cap, its passage and/or seal act as a die to cooperate with the punch to facilitate a shear action removal of the sample.

As shown where the first end of the storage container 500 comprises a cap 550 with a seal 557 as described above, the collector 250 is pushed into the recess 555 formed in the cap. Optionally, the wall of the recess comprises one or more ribs for engaging with the guiding ribs 254 of the punch to guide the body of the punch within the cap. As the collector pushes into the cap, the cutting edge 255*a* of the punch presses against and then pierces the seal or membrane 557 to form an opening to the storage body. The cutting end of the punch (holding the plunger therein) is then pushed through the opening so that the sample holding region 256, and the sample 460 held within the cavity 256, is located within the body of the storage container 500. The collector fills the opening formed by the broken seal to close off the first end of the container. In particular, the size of the punch is sized to fit snugly and preferably sealingly within the opening formed in the cap so that the cap is able to hold the collector therein. Preferably, the second end of the plunger projects from the pushing end of the punch and the first end of the plunger is located within the bore of the punch between the sample holding cavity and the pushing end of the punch. In this arrangement, the plunger can be depressed and pushed through the sample holding region to release the tissue sample into the storage container. This may occur manually or by tool and may be done at sampling or after.

When the collector closes off the first end of the storage container, the punch and the plunger are held by the cap of the storage container so that the cutter is held within the container body. It remains so during transport to a laboratory. It is therefore not necessary for the user of the sampler to handle the punch with its sharp cutting edge or to otherwise remove and discard the punch from the tissue sampler.

The trigger mechanism of the sampler 1 is such that the action of cutting the tissue sample, placing the sample in the storage container, and releasing the animal's ear is almost instantaneous so that if the animal reacts to having its ear cut and pulls away, there is little chance that the animal can pull the tissue sampler from the user's hand before the ear is released.

With reference to FIGS. 21 to 26 a variation is shown where provision is made to help avoid cross contamination between samples. Such cross contamination is avoided by the provision of a shield 900 that separates the ram from coming into contact with the tissue surfaces. In the preferred form a shield 900 and a collector 250 are associated with each other in a chamber of a magazine. The association is severable and may be such as to be established by way of friction or other contact. The ram 130 is able to engage with the shield 900 and/or the collector 250 to drive the collector through the tissue sample. The shield 900 provides an extension and/or a shroud around the ram to prevent the ram from contacting the tissue that is so cut by the collector. In the preferred from the shield 900 acts as an extension so that the ram does not penetrate through or at least partially into the tissue that is being sampled. Upon being driven by the ram 130 both the shield and the collector 250 advance towards the storage container. The collector 250 is driven into the storage container in a manner as has hereinbefore been described. Once it reaches its engaged condition with the storage container the ram moves back to its withdrawn position and takes with it the shield 900. The shield 900 is retracted back into the chamber of the magazine and by way of a stop is separated from the ram 130 as the ram retracts to its withdrawn position, leaving the shield 900 in the magazine chamber. Whilst in the preferred form the shield and collector is provided located in a magazine of a plurality of shields and collectors it is envisaged that single shot assemblies of a collector and shield may be provided. The advantage of a magazine located collector and shield is that once all of the collectors have been dispensed from the magazine the retracted shields are then retained by the magazine and can be disposed of in an appropriate manner as a single unit. Engagement between the ram and shield may be through a tapered relationship or a barb or other formation such as that shown in FIG. 22*b* may be provided to facilitate such association and ensure full retraction of the shield back to the chamber of the magazine upon the withdrawal of the ram to its withdrawn position.

The storage container, including the cap holding the collector can then be removed from the holder and an unused replacement storage container can then be fitted into the holder. The collector magazine is rotated incrementally until the next chamber containing an unused collector is aligned with the ram receiving aperture and cutting region aperture, ready for another tissue sample to be taken.

Once all the collectors in the magazine have been used the magazine can be removed from the sampler 1.

Figure 12:
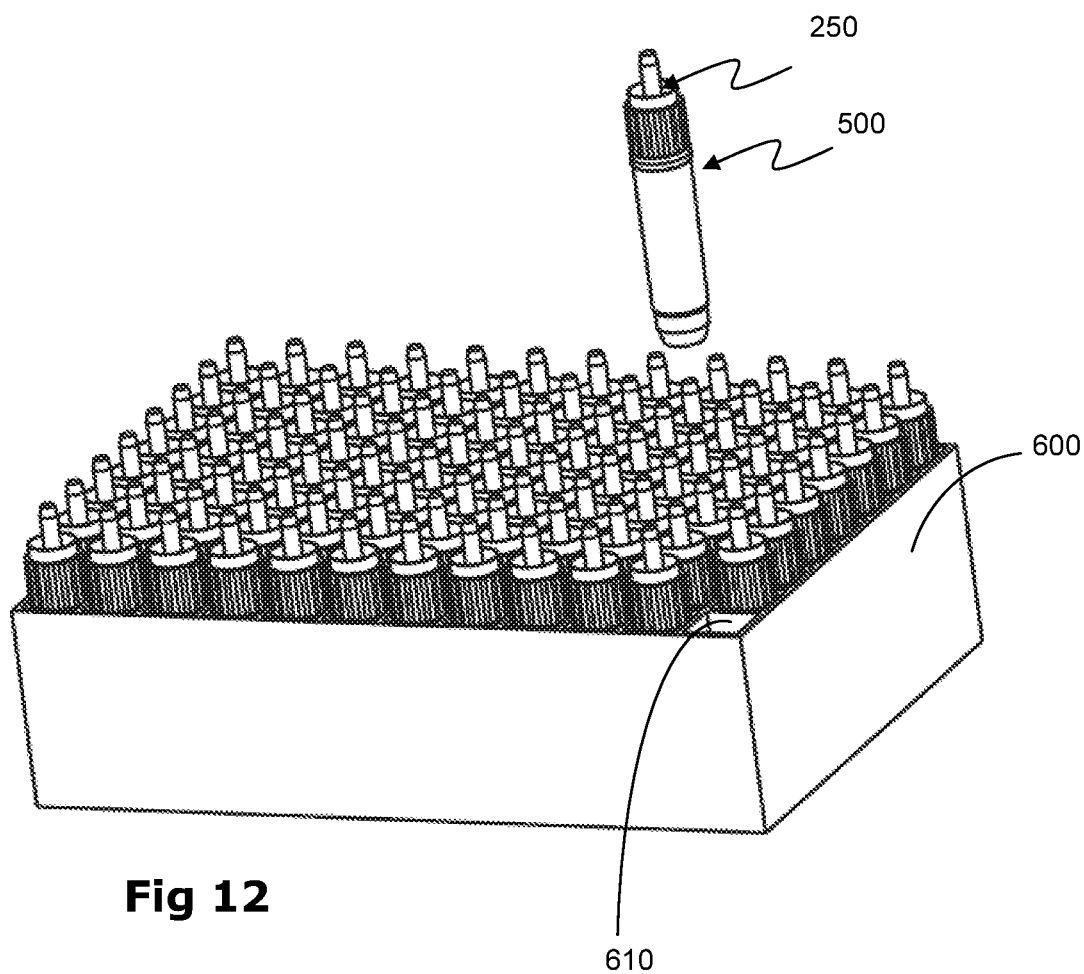
FIG. 12 is a perspective view of a plurality of collectors held within a multi-cell rack.

Preferably, the storage containers removed from the tissue sampler are placed within respective cells 610 of a multi-cell rack 600, such as a 96 well rack as shown in FIG. 12, before being sent to a laboratory for decapping and future analysis of the samples.

The collector is adapted so that the plunger can be pushed to release the tissue sample from the sample holding region and into the tissue chamber at the bottom of the container. In particular, the second end of the plunger can be depressed toward the pushing end of the punch to cause the first end of the plunger to push a tissue sample out of the sample holding region and into the body of the storage container. To assist with the release of the tissue sample, the first end of the plunger may be enlarged and may comprise an anti-stick surface formed of a non-stick material, such as Teflon™. The plunger may be depressed and pushed towards the sample holding region after the container has been removed from a tissue sampler.

Preferably, the tissue sample is held at the sample holding region when the storage container is removed from the tissue sampler. The storage containers may then be placed within respective cells of a multi-cell rack so that the base of each storage containers is at the bottom of the respective cell and the caps of the storage containers project above the cells, as shown in FIG. 12. The diameter or width of the cells is sized to be commensurate with the diameter or width of the storage containers.

Figure 13:
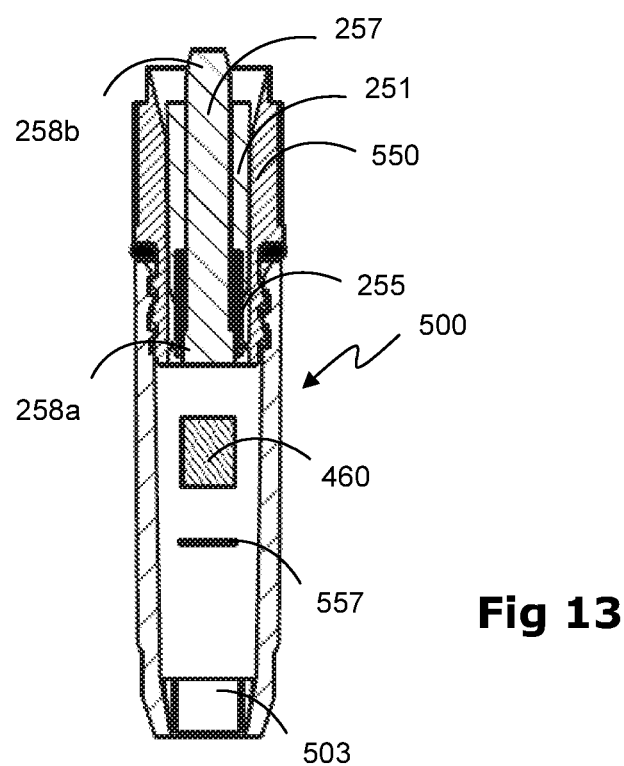
FIG. 13 is a cross-sectional side view of the storage container in which the tissue sample has been released from the collector.
Figure 14:
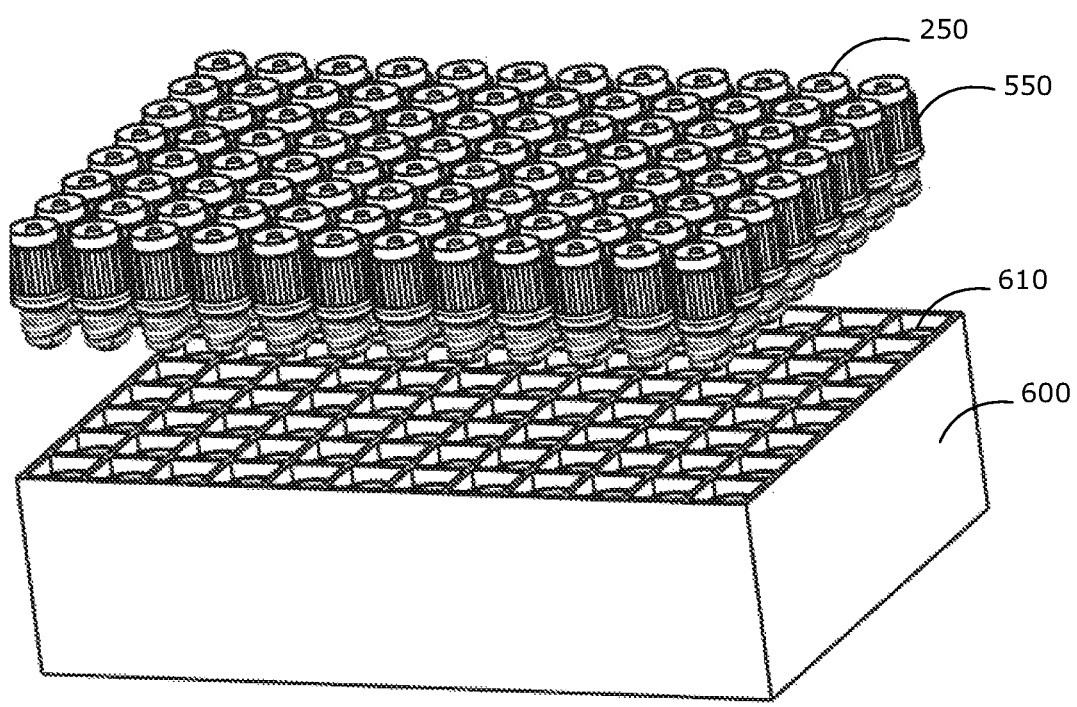
FIG. 14 is a schematic perspective view showing a plurality of storage containers being decapped simultaneously.
Figure 15A:
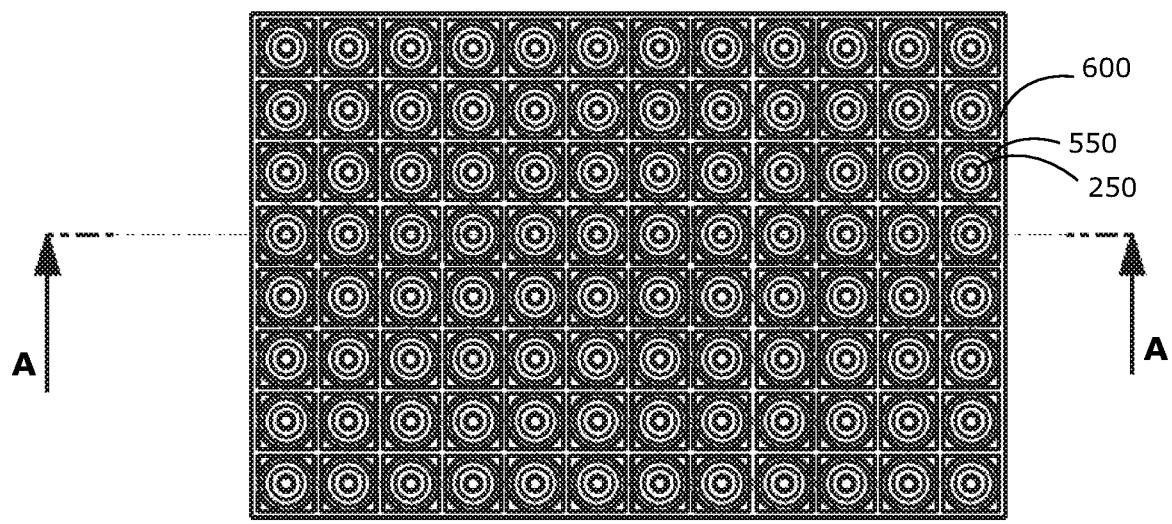
FIG. 15a is a top vies of the decapped storage containers of FIG. 14.
Figure 15B:
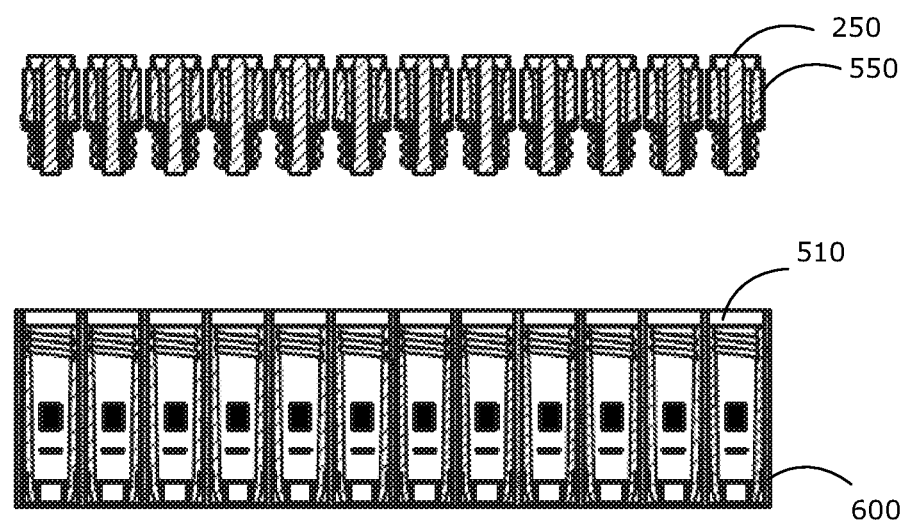
Figure 15C:
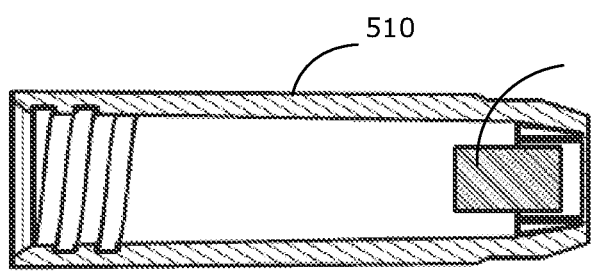
FIG. 15c is a cross sectional side of a single storage container after being decapped.
Figure 16:
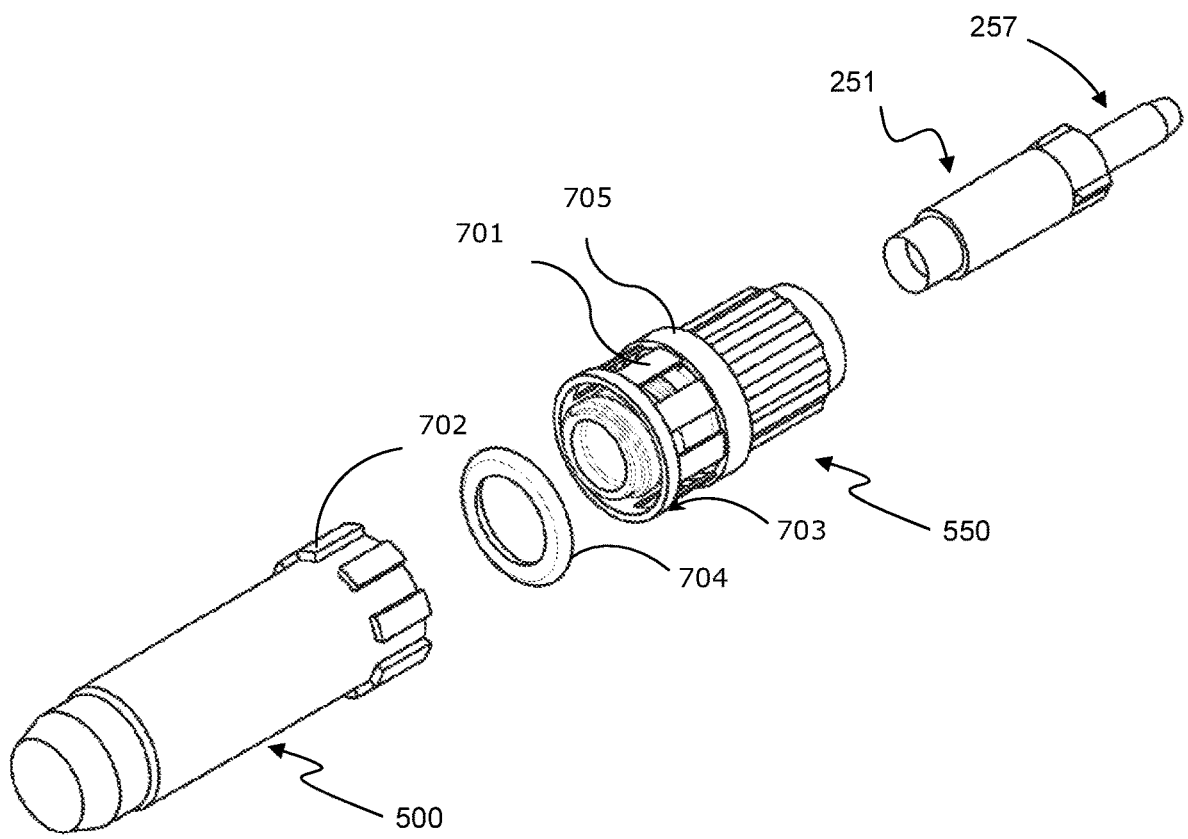
FIG. 16 is an exploded perspective view of a tamperproof collector and associated storage container.

A machine may be used to depress the plungers within the caps of the storage containers automatically, either by depressing the plunger consecutively or by simultaneously depressing the plungers of all in the rack. As each plunger is depressed and pushed deeper into or through the bore of the punch and through the sample holding region toward the base of the storage containers, the sample is pushed from the sample holding region and is deposited into the chamber at the bottom of the storage containers, as shown in FIG. 13. The tool so used in the lab does not contact the sample.

Where the outer surface of the body of each storage containers comprises anti-rotation means, the storage containers are located within the respective cells of the holder so that the anti-rotation means engage with corresponding anti-rotation means provided within the cells. For example, one or more projections formed on a container body will engage with one or more recesses formed in the walls of the respective cell. The anti-rotation means of the storage containers and cells prevent the tubes from rotating within the cells so that the storage containers can be automatically decapped by unscrewing the caps from the body.

To decap the storage containers, a cap engaging tool (not shown) engages with the correspondingly shaped recess of the cap, or to grip onto the outer surface of the guide wall of the cap, and is rotated in the appropriate direction to unscrew the cap from the storage container. Typically, a machine is provided in which multiple cap engaging tools engage with the caps of multiple storage containers in a rack to decap the storage containers of the rack simultaneously, as shown in FIGS. 14, 15*a-c*.

Decapping will result in the tamper evident indicator breaking or rupturing. This is preferably achieved in the process of de-capping and not by a separate step. For example an unscrewing of the cap from the container body will result in the simultaneous breaking or rupturing of the tamper evident indicator. The tamper evident indicator provides little of no resistance to the separating of the cap from the container.

Decapping the storage containers enables the samples to be accessed. The samples are preferably located in the bottom of the containers or may still be retained by the collector and subsequently dispensed into a test tube by a pushing of the plunger. Laboratory testing of the sample may occur in the storage container itself or alternatively the sample is removed from the container or cutter before testing.

The lab can process the sample in lab tubes that may receive the samples direct from the collector if still retained by the collector after decapping (samples are pushed off the punch by the plunger) or from the storage container bodies. The RFID tag of the collector or ID from the container body can be matched or transferred or recorded relative a lab system number for the lab tube that the sample is deposited in. This can give flexibility if larger processing tubes are required and the sample can then be pushed into any make of tube.

Optionally, the base of each storage container and/or the rack may be adapted to provide a tube lock feature in which the storage container is locked in place within a respective cell. The storage container may locked within the cell in any suitable arrangement. For example, the exterior of the storage container may be threaded to engage with a threaded interior of the cell or the storage container may be adapted to snugly fit or snap-fit into a cell of a rack. Once the storage container is locked within the cell, the storage container is held in place even if the rack is inverted. By using this feature, the rack can be inverted to eject the samples from the storage containers.

Optionally, each cell within the rack comprises an open or transparent bottom for reading unique indicia located on the base of each storage container held within the rack so that the source of each sample can be identified and linked with the data obtained from the sample.

Advantages

After sampling the cap will continue to hold the used collector. It can then be easily disposed together with the cap once the sample has been ejected from the collector.

The storage container can receive and hold the biopsy collector and avoids the need for the user to handle and/or dispose of used punches at the time of sampling. The biopsy collector is held by the storage container after a sample is taken, so it is not necessary for the sampler user to handle and/or dispose of the used punch. The collector and its punch stay connected to the storage container after sampling reducing or eliminating waste at time of sampling. The sample can remain held by the cutter and be deliberately ejected from the cutter such as into a storage container at will. Not just at the time of sampling. The cutter retained sample is protected by the cutter and this will reduce sample drying or contamination. The cutter can retain the sample so that it does not contact the container body.

The tamper evident indication allows visual inspection of tampering with any sample in the container.

Although the invention has been described by way of example, it should be appreciated that variations and modifications may be made without departing from the scope of the invention as defined in the claims. Furthermore, where known equivalents exist to specific features, such equivalents are incorporated as if specifically referred in this specification.

The invention claimed is:

1. A storage container to receive and store a biopsy sample of an organism, said biopsy sample being held by a biopsy sample collector, said storage container comprising:
   a. a container body defining a containment region with an open end,
   b. a container cap removably located relative to the container body and threadingly engaged to the container body at the open end to seal the containment region, the container cap including a passage formed by an annular flange extending away from the open end, the passage comprising a closure at one end of the passage adjacent the open end, and an opening at an opposite end of the passage opposite the closure, wherein the closure is configured to be ruptured by the biopsy sample collector to allow the biopsy sample retaining biopsy sample collector to thereafter enter the containment region so that the biopsy sample can be stored in the containment region and wherein said biopsy sample collector can be retained by said container cap and seal the passage, wherein the closure is integrally formed with the cap and fully seals the end of the passage prior to rupture,
   wherein the container cap presents a sample cutting surface adjacent the passage opening to cooperate with the sample collector in cutting a sample from the organism to be sampled, and the sample cutting surface arranged to allow the sample collector to pass by the sample cutting surface and through the passage opening and into the passage in a shearing action to facilitate in removal of said biopsy sample, wherein the cap is configured to receive the biopsy sample collector and hold said biopsy sample collector after rupturing of said closure and entry of said sample into the containment region, and the storage container comprises a tamper evident indicator configured to indicate if separation of the cap from the container body occurs.

2. A storage container as claimed in claim 1 wherein the closure of the cap is a membrane.

3. A storage container as claimed in claim 1 wherein the closure is able to separate from the cap upon rupturing.

4. A storage container as claimed in claim 1 wherein the closure is able split open upon rupturing yet at least in part be retained to said cap.

5. A storage container as claimed in claim 1 wherein the cap is adapted and configured to prevent the biopsy sample collector from being removed there from after rupturing of said closure and entry of said sample into the containment region.

6. A storage container as claimed in claim 1 wherein the passage is shaped and dimensioned to result in a wedging of the biopsy sample collector therein to prevent the removal of the biopsy sample collector from the cap after rupturing of said closure and entry of said sample into the containment region.

7. A storage container as claimed in claim 1 wherein the tamper evident indicator is a tamper evident ring that is integrally formed with one of the container body and cap and is engaged to the other of said cap or container body in a manner so that upon separation of the cap from the container body, the ring at least in part becomes disconnected from the container body or cap with which it is integrally formed.

8. A storage container as claimed in claim 1 wherein at least one of the container body and cap includes at least one of an EID and machine readable code (such as a barcode).

9. A storage container as claimed in claim 1 wherein the storage container is a storage container to receive and store a biopsy sample storage container.

* * * * *